(12) United States Patent
Kelly et al.

(10) Patent No.: US 6,863,866 B2
(45) Date of Patent: Mar. 8, 2005

(54) SELF-CONTAINED DEVICES FOR DETECTING BIOLOGICAL CONTAMINANTS

(75) Inventors: Tim Allen Kelly, Bellevue, WA (US); George Michael Hass, Sammamish, WA (US); Philip Thomas Feldsine, Mercer Island, WA (US)

(73) Assignee: BioControl Systems, Inc., Bellevue, WA (US)

( * ) Notice: Subject to any disclaimer, the term of this patent is extended or adjusted under 35 U.S.C. 154(b) by 462 days.

(21) Appl. No.: 09/874,913

(22) Filed: Jun. 4, 2001

(65) Prior Publication Data

US 2002/0057991 A1 May 16, 2002

Related U.S. Application Data

(60) Provisional application No. 60/208,865, filed on Jun. 2, 2000.

(51) Int. Cl.[7] .......................... G01N 21/77; G01N 31/22
(52) U.S. Cl. .............................. 422/56; 422/55; 422/58; 436/164; 436/169; 436/86
(58) Field of Search ....................... 422/55, 56, 58–61; 436/164, 169, 170, 86, 800

(56) References Cited

U.S. PATENT DOCUMENTS

| | | | |
|---|---|---|---|
| 3,485,587 A | 12/1969 | Keston ........................ | 23/230 |
| 3,792,699 A | 2/1974 | Tobin et al. ................ | 128/2 W |
| 4,707,450 A | 11/1987 | Nason ........................ | 435/295 |
| 4,978,504 A | 12/1990 | Nason ........................ | 422/61 |
| 5,266,266 A | 11/1993 | Nason ........................ | 422/58 |
| 5,304,468 A | 4/1994 | Phillips et al. ................ | 435/14 |
| 5,424,000 A | 6/1995 | Winicov et al. ............ | 252/151 |
| 5,550,061 A * | 8/1996 | Stone .......................... | 436/73 |
| 5,726,062 A | 3/1998 | Numa et al. .................. | 436/86 |
| 6,551,834 B2 * | 4/2003 | Carpenter et al. ............ | 436/86 |

FOREIGN PATENT DOCUMENTS

| | | |
|---|---|---|
| EP | 734 686 A1 | 10/1996 |
| EP | 806 666 B1 | 11/1997 |
| WO | WO 96/14570 | 5/1996 |
| WO | WO 00/09016 | 2/2000 |

OTHER PUBLICATIONS

Neuhoff et al., "Clear background and highly sensitive protein staining with Coomassie Blue dyes in polyacrylamide gels: A systematic analysis," *Electrophoresis* 6: 427–448, 1985.

Neuhoff et al., "Improved staining of proteins in polyacrylamide gels including isoelectric focusing gels with clear background at nanogram sensitivity using Coomassie Brilliant Blue G–250 and R–250," *Electrophoresis* 9: 255–262, 1988.

* cited by examiner

Primary Examiner—Maureen M. Wallenhorst
(74) Attorney, Agent, or Firm—Seed Intellectual Property Law Group PLLC

(57) ABSTRACT

The present invention relates generally to self-contained devices and methods for detecting biological contaminants and, more particularly, to self-contained devices and methods for detecting biological contaminants in relevant settings including, for example, food processing plants, hospitals, medical offices, veterinary offices, and restaurants by using a device or methodology that includes a sampler component and dye component that binds to the biological material in a detectable fashion.

14 Claims, 11 Drawing Sheets

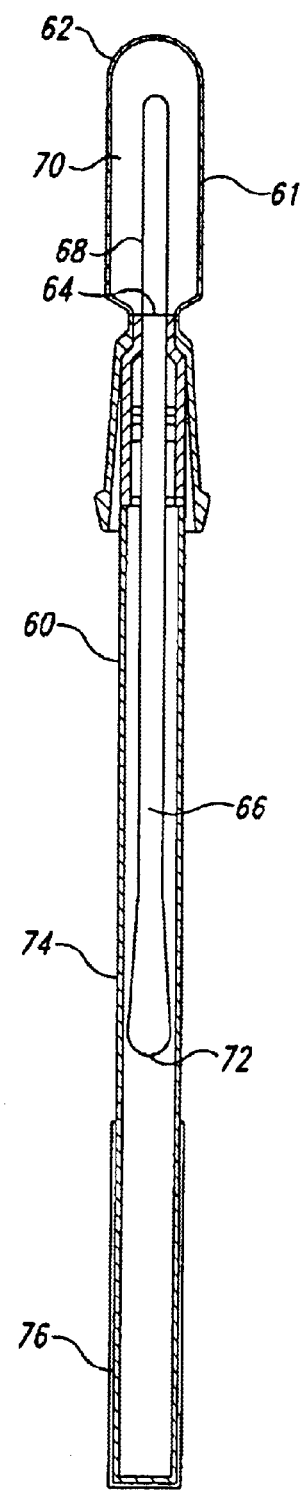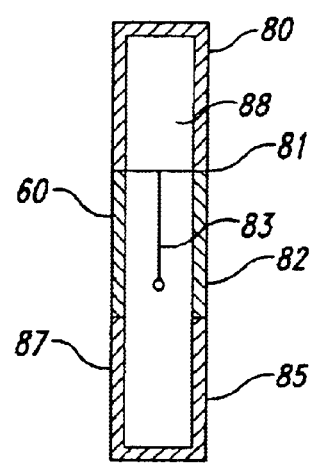
Fig. 6
Fig. 7

SELF-CONTAINED DEVICES FOR DETECTING BIOLOGICAL CONTAMINANTS

CROSS-REFERENCE TO RELATED APPLICATION

The present application claims priority to U.S Provisional Application No. 60/208,865, filed Jun. 2, 2000.

TECHNICAL FIELD

The present invention relates generally to self-contained devices and methods for detecting biological contaminants and, more particularly, to self-contained devices and methods for detecting biological contaminants in relevant settings including food processing plants, hospitals, medical offices, veterinary offices, and restaurants by using a device or methodology that includes a sampler component and dye component that binds to the biological material in a detectable fashion.

BACKGROUND OF THE INVENTION

This invention relates to the field of testing for biological contaminants. Such contaminants may be found on equipment or other surfaces used in environments including food processing plants, hospitals, veterinary offices, and restaurants when a thorough cleaning has not been performed. Materials detected as indicators of contamination include, for example, viable bacterial cells, viruses, ATP, and protein. The ideal test for contamination would be effective, inexpensive, rapid, and easy to use and interpret.

Although pathogenic bacteria and viruses are clearly hazardous, the commonly used methods to detect them involve a number of steps, such as reagent preparation, reagent mixing, sample transfer, sample/reagent mixing, and incubation prior to reading results. Tests for these materials are not only time consuming but they also typically require the use of expensive and complicated equipment. Thus, routine testing of surfaces or equipment directly for bacteria or viruses is not practical in settings in which the testing is done by non-technical personnel and rapid results are demanded. As an alternative to testing for bacteria and viruses, many food processing plants use surrogate markers such as ATP and protein as indicators of contamination. Although these substances themselves are not usually harmful, they may serve as nutrient material for bacteria and are good general indicators of the effectiveness of cleaning.

ATP (adenosine triphosphate) is a chemical common to all living organisms. The presence of significant levels of ATP on a surface indicates that cleaning was incomplete and that bacteria may be present. Because hygiene monitoring by ATP detection is common, relatively inexpensive, rapid, and effective, it is widely used. However, detecting ATP suffers from certain limitations that restrict its utility, in that it involves the use of a relatively expensive instrument and may involve transporting samples to a central laboratory.

Clearly tests for protein as evidence of contamination provide an attractive alternative to direct testing for bacteria and viruses or for ATP detection. Unfortunately, many examples of current methods for protein determination, which can serve as an indicator of a contaminated surface involve on-site reagent preparation due to stability problems, along with multiple transfer steps, incubation periods, and/or involve highly subjective color changes which make interpretation difficult, and/or require the use of complex instrumentation or specially trained personnel.

Examples of common protein determination methods are described in Stoscheck, *Quantitation of Protein*, in METHODS IN ENZYMOLOGY Vol. 182, pp.50–68, 1990. Among the variants of basic protein detection methods are methods using colloidal forms of COOMASSIE® blue stain to detect proteins in gels such as polyacrylamide electrophoresis gels. Such methods are described, for example, in Neuhoff et al., *Electrophoresis* 6:427–488, 1985 and Neuhoff et al., *Electrophorests* 9:255–262, 1988. In addition to the conventional protein assay methods referenced above, a combination cleaning and protein staining composition is described in Winicov et al., U.S. Pat. No. 5,424,000, entitled ACID CLEANINGS AND STAINING COMPOSITIONS, issued Jun. 13, 1995. The solutions preferably include phosphoric, sulfuric, and nitric acids, and Acid Violet 19 dye.

A number of different self-contained sampling/testing devices employing certain assays have been described. Examples of such assays include sampling for bacterial contaminants in food processing plants, the sampling for contamination of the environment by heavy metals such as lead, and the collection of specimens from a patient to test for microorganism infection.

Specific examples of self-contained sampling/testing devices include Nason, U.S. Pat. No. 5,266,266, issued Nov. 30, 1993, and Nason, U.S. Pat. No. 4,978,504, issued Dec. 18, 1990, both entitled SPECIMEN TEST UNIT; Nason, U.S. Pat. No. 4,707,450, issued Nov. 17, 1987, entitled SPECIMEN COLLECTION AND TEST UNIT; Numa, U.S. Pat. No. 5,726,062, issued Mar. 10, 1998; and Tobin, U.S. Pat. No. 3,792,699, issued Feb. 19, 1974. The use of protein error dyes to estimate protein content in urine is disclosed in Keston, U.S. Pat. No. 3,485,587, entitled PROTEIN INDICATOR. All of which are hereby incorporated by reference in their entireties including drawings. However, all of the aforementioned devices suffer from the same drawbacks noted above.

Thus, as no self-contained device or methodology exists that is inexpensive, rapid, and easy to use and interpret, there exists a need in the art for such a device relevant to the detection of biological contamination. The present invention fulfills these needs, and provides other related advantages.

SUMMARY OF THE INVENTION

The present invention generally provides novel methods and self-contained devices for detecting biological contaminants in a variety of settings. In one aspect, provided is a self-contained sampling/testing device having a sampler for collecting target material and a signal generator comprising a dye which binds to said target material to signal the presence of said target material. In one embodiment the device also contains a sampler washer having a wash solution. In other embodiments, the device has an absorbent material, wherein the sampler has a porous sample collection pad, and the absorbent material, the sampler, and the sampler washer are configured and arranged such that the sample collection pad can be disposed between the absorbent material and the sampler washer so that the wash solution separates dye bound to said target material immobilized on said sample collection pad from unbound dye.

Also included are embodiments wherein the sampler has a porous sample collection pad for collecting the target material, wherein the dye and the wash solution are contained in a reagent tray housing capable of being contacted by the sampler to impart the dye and the wash solution across the target material contained on the sampler. Further embodiments include a device wherein the dye and the wash solution are contained in a plurality of reservoirs, wherein the reservoirs are serially contacted by the sampler to first expose the target material to the dye and then to wash unbound dye away from bound dye. In related embodiments the device may contain a wetting agent for moistening said sample collection pad in advance of collecting said target material. Further, the wetting agent may be the same as or differ from the wash solution.

In yet other embodiments the device has a sampler that is hollow and wherein the absorbent material is disposed within the sampler to facilitate transport of the dye and the wash solution across the target material or the wash solution is disposed within the sampler.

In one embodiment the device comprises a reagent housing comprising an absorbent material, wherein one of the absorbent materials is saturated with the wash solution, and the other of the absorbent materials is unsaturated, wherein unbound dye from a sampler collection surface disposed there between is washed by the flow of the wash solution from the saturated absorbent material to unsaturated absorbent material. In addition, the dye may be transported by the wash solution to the target material to effect the binding. Further, the device may contain at least one rupturable membrane. This membrane may separate any component such as wetting solution from the absorbent material, dye from the absorbent material, or wash solution from the absorbent material. In certain embodiments the dyes utilized may be protein binding dyes such as Ponceau-S and in other embodiments dyes which either precipitate and stain target material or change color (frequency shift) upon binding target material.

In other embodiments the device contains a dye in a dry form until contacted by a wetting agent or sample. In still other embodiments the device may contain a neutralizing agent to neutralize any compounds in the sample that might interfere with the binding of the dye to the target material. In certain embodiments the neutralizing agent is sodium thiosulfate, $MgCl_2$, sodium dodecyl sulfate, tergitol, Triton X-100, or Tween 20. In yet other embodiments the dye is a frequency shift dye or colloidal dye. In specific embodiments these dyes may be Coomassie dyes or bromophenol blue.

In the various embodiments, the sampler is contained within a lower housing providing protection from pre-testing contamination for the sampler, the device further comprising an upper housing, wherein the upper housing and the lower housing sealably engage, and the sampler is attached to the upper housing. In other embodiments the sampler of the device contains an absorbent pad at the surface of which is positioned a membrane to which a dye is attached either covalently or non covalently or in the alternative the dye is attached directly to the absorbent pad and/or the no membrane is present.

In other aspects the device contains a wetting/neutralizing solution that is contained within a reagent housing containing an absorbent material. In further embodiments the sampler contains an absorbent material which is pre moistened with wetting/neutralizing solution. In the alternative the sampler contains a breakable vial or rupturable compartment containing wetting/neutralizing solution. Further, the device of the invention may contain a frequency shift dye of the protein error family, such as bromophenol blue. In further embodiments, the wetting/neutralizing solution may be sodium thiosulfate, $MgCl_2$, sodium dodecyl sulfate, tergitol, Triton X-100, or Tween 20.

In a further aspect, a self-contained sampling/testing device is provided which comprises a sampler for collecting biological target material and a signal generator comprising a frequency shift dye of the protein error family, the dye being capable of binding to the biological target material and producing a color change upon binding to the target material wherein unbound frequency shift dye need not be separated from biological target bound frequency shift dye in order to detect the presence of target material. In related embodiments the device contains at least one of the following: an absorbent material and/or a wetting agent. In certain embodiments the dye is bromophenol blue, while in other embodiments the device contains a wetting solution that contains a neutralizing agent such as one or more of sodium thiosulfate, $MgCl_2$, sodium dodecyl sulfate, tergitol, Triton X-100, or Tween 20.

These and other aspects of the present invention will become evident upon reference to the following detailed description and examples. In addition, the various references set forth below describe in more detail certain procedures or compositions (e.g., dyes, detection methodologies, etc.), and are therefore each incorporated herein, by reference, in their entirety.

BRIEF DESCRIPTION OF THE DRAWINGS

FIG. 6 illustrates an embodiment in the published art containing a swab-type sampler in which the dye solution in the sampler portion also functions as the sampler wash solution.

FIG. 7 illustrates an embodiment in the published art of a device in which the housing is divided into an upper housing portion and a lower housing portion which sealably engage, in which the lower portion of the lower housing is set off by a separator.

The lower portion of the device (the housing), protects the sampler when the two portions of the device are sealed together. The housing also contains a separator which divides the housing into upper and lower spaces. The lower space contains a dye composition, preferably a dry dye.

Figure 9:
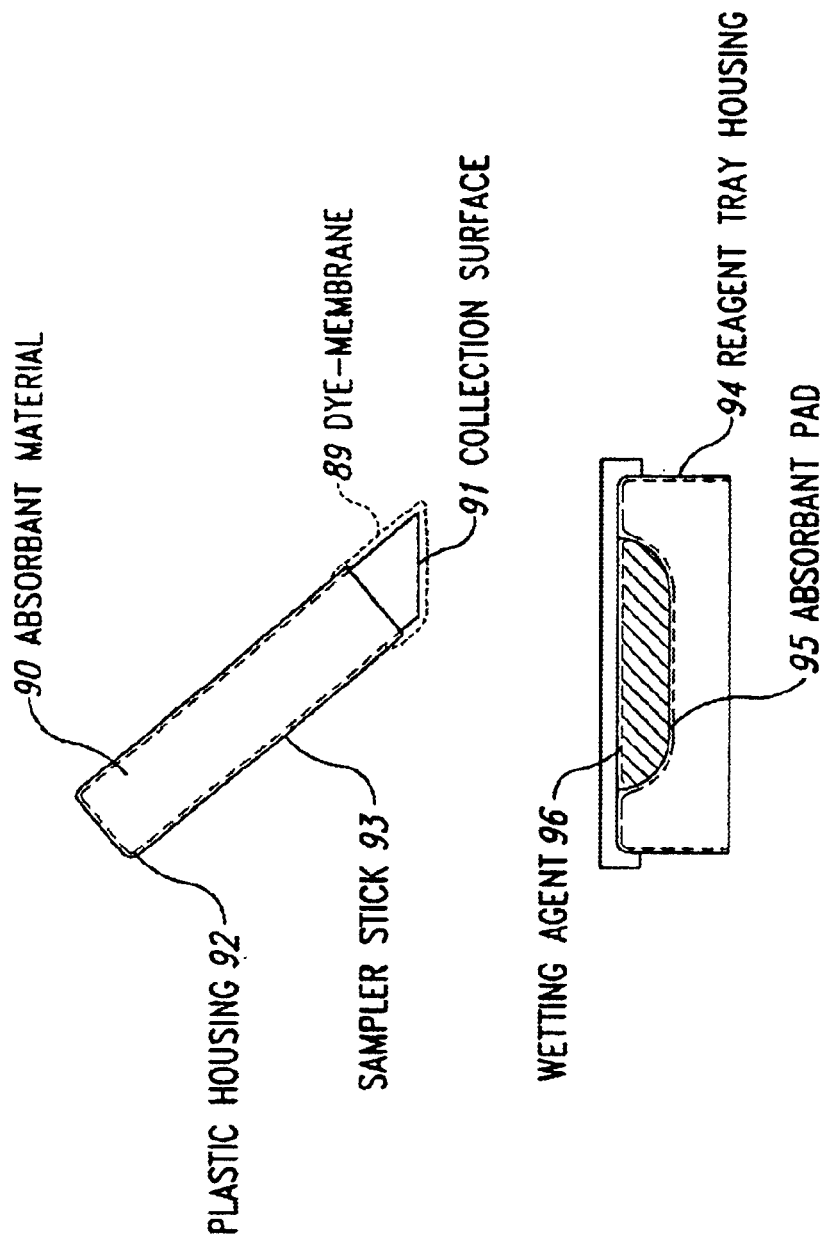

FIG. 9 illustrates an embodiment of the inventive device in which the dye is bound to a membrane on the surface of the sampler. The wetting solution is contained in a separate reservoir.

Figure 10:
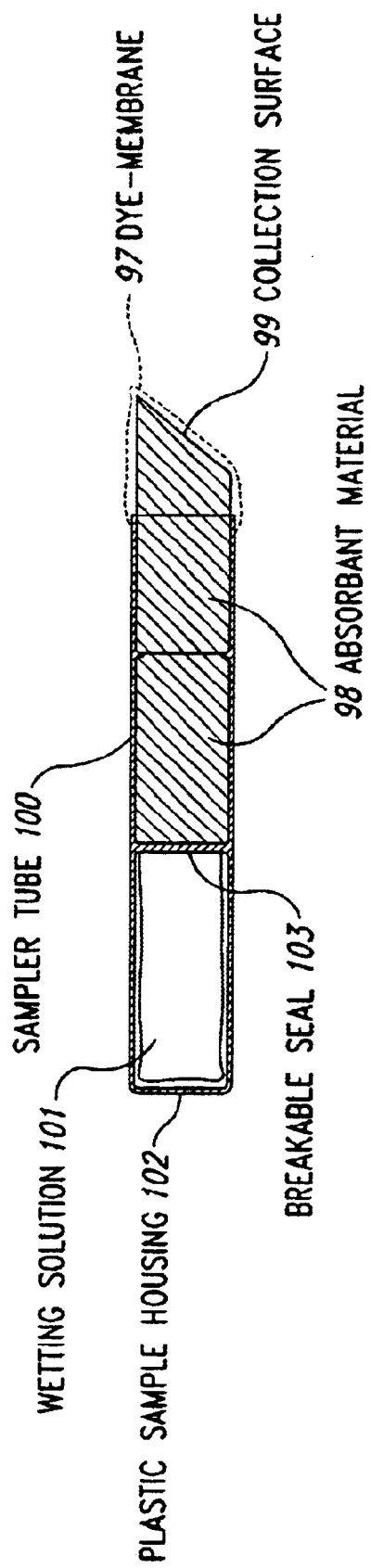

FIG. 10 illustrates an embodiment of the inventive device in which the dye is also bound to the surface of the membrane and the wetting agent is contained in a compartment separating it from the absorbent material/dye-membrane by a breakable seal.

Figure 11:
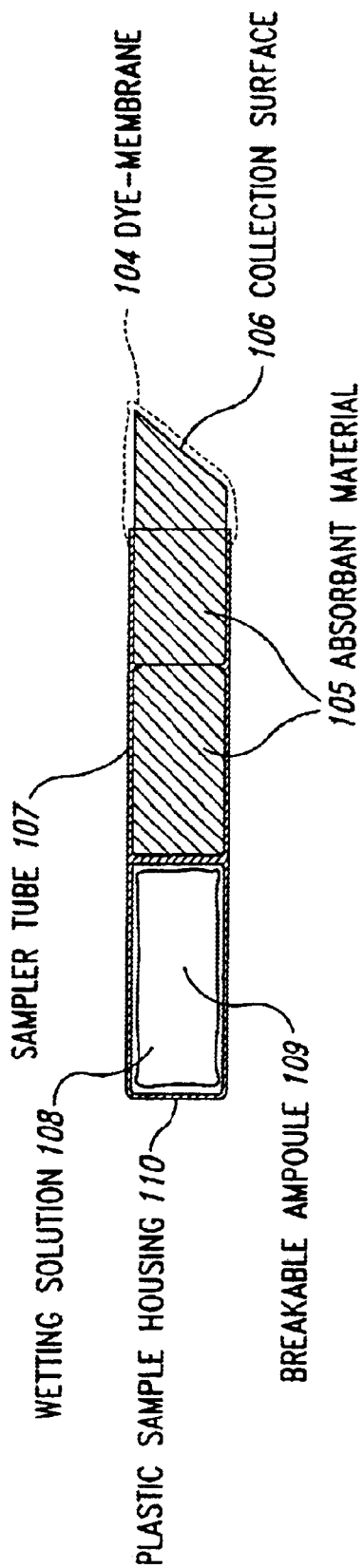

FIG. 11 illustrates an embodiment of the inventive device in which the dye is bound to a membrane at the surface of the sampler and the wetting agent is stored in a rupturable ampoule within the plastic housing of the sampler stick.

Figure 12:
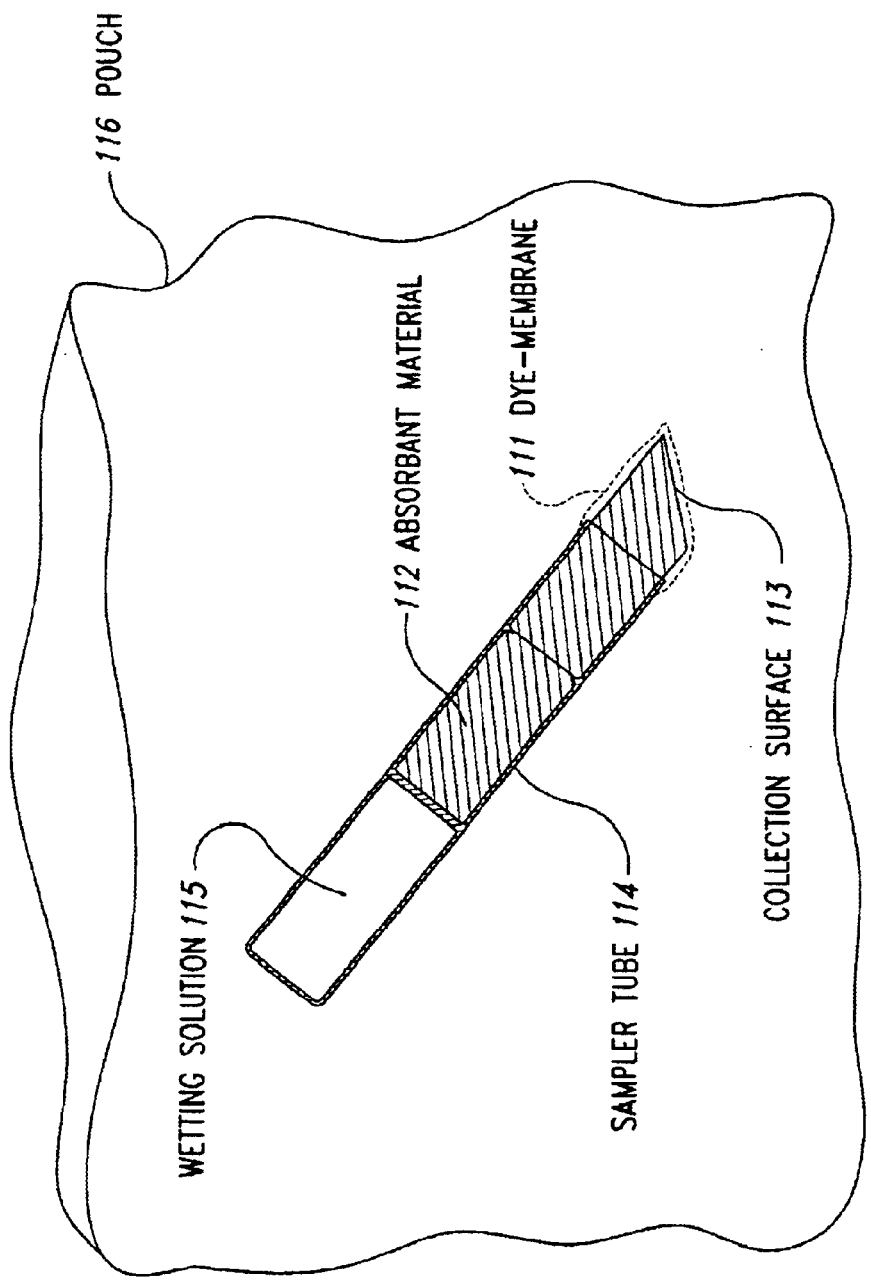

FIG. 12 illustrates an embodiment of the inventive device in which the dye is bound to a membrane at the surface of the sampler and the wetting agent is contained in the absorbent material within the sampler stick and each device is sealed in a foil pouch to prevent evaporation of the wetting agent.

DETAILED DESCRIPTION OF THE INVENTION

The device and methods of the present invention are self-contained, inexpensive, rapid, and easy to use and interpret. In certain embodiments, the device and methods utilize a dye that changes color in the presence of significant amounts of protein (i.e., a protein error dye or polychromatic dye, see Keston et al., Supra) attached at or near the surface of a sampling stick and in further embodiments the device or method contains a means for wetting the sampling surface prior to contact with the test surface. Such means for wetting can be provided by a wetting agent/solution which aids in protein solubilization, neutralizes contaminants that might interfere with protein detection, and maximizes detection of target material.

The need for, and utility of on site, immediate feedback to cleaning and audit personnel on the presence of residual contaminating substances in a variety of environments is well-established. For example, the need for contaminant monitoring has a well-documented role in food safety programs when residual food residues can result in bacterial contamination and allergic responses in some individuals. Effective cleaning also reduces the risk of pathogens contaminating subsequent food products. A variety of devices and methods have been utilized for contaminant testing. Similarly, there is a need to ensure that surfaces and equipment in hospitals, physicians' offices, clinical laboratories, or veterinarian offices have been adequately cleaned to protect patients and staff.

Particularly advantageous devices for the purpose of evaluating the presence of specific materials require no secondary reagents or steps, have easily detected changes in the presence of target material, give immediate results, and allow integrated collection of sample into the device. The present invention demonstrates that such a self-contained sampling/testing device can be constructed in which the presence of target material in a sample is detected colorimetrically through use of a dye which binds the target material. As indicated above, this device is particularly advantageous for routine sanitation testing procedures.

In a first aspect, the present invention concerns a self-contained device having a sampler for collecting a sample which may contain a target material and a signal generator having a contactable dye that binds to the collected target material. In certain embodiments, the device may contain a sampler washer having a wash solution for washing the collected target material and/or free dye from or on the sampler to facilitate measurement of a signal produced from the interaction of dye and target material. In other related embodiments the device or method has a reservoir capable of providing a wetting agent to the sampler. The sample collection surface portion of the sampler is in communication with or can be placed in communication with the sampler washer or sampler wetting agent. In certain embodiments, the sampler collection surface is also in communication with or can be placed in communication with an absorbent material able to take up liquid from a wetting agent and/or dye solution and/or wash solution. The device may be constructed with any of many possible structural configurations, depending on the requirements of the particular application, e.g., depending on the specific type of dye used and the type of target material to be tested.

The term "in communication," as used herein, refers to a contact or channel or other means that allows fluid contact between the referenced components. Thus, for example, a sampler washer and an absorbent material are in communication if fluid transport can occur from the sampler washer or wetting agent reservoir into the absorbent material. The term does not imply that fluid is actually present, but only that such fluid contact could occur if fluid were present.

In certain embodiments, the device incorporates a target material precipitating dye, preferably a protein precipitating dye, for example, Ponceau-S dye. Such a dye binds to and precipitates, or assists in precipitating or keeping out of solution a target material. The sample collection surface of the sampler can be contacted with the dye (in solution or dry) in a manner such that a quantity sufficient to dye target material in a sample is taken up by the sampler. In using such dyes, it is generally advantageous but not required to separate bound dye from unbound dye to provide convenient detection of the presence of target material. Thus, embodiments using such dyes may employ an arrangement where the collected sample (which may contain target material) is or can be disposed between reservoirs such that wash solution can pass through or over a solid matrix carrying the collected sample. For example, the collected sample can be disposed between an absorbent material able to absorb wash solution and an absorbent material or other reservoir containing a wash solution. The saturation differential between these reservoirs provides for a directional transport of dye and wash solution across the collection pad surface. Preferably the wash solution is drawn through or over a matrix bearing a collected sample by capillary action. In embodiments where the collection surface and dry absorbent material are in direct contact, the dry absorbent material should have at least enough capacity to absorb sufficient dye and wash solution to wash the sample collection surface. In other embodiments, rather than involving capillary action in an absorbent material to draw wash solution through a sample-bearing matrix, a wash utilizes user-applied pressure that pushes wash solution through the sample-bearing matrix.

The term "matrix" refers to a solid material suitable for retaining dye/target material complexes. In the context of this invention, a matrix is preferably, but not necessarily a porous matrix or porous material, meaning that the matrix is penetrated by a large number of passages of sufficient size to accept the passage of fluids such as water, but are preferably not so large that the matrix is free-draining. Such a porous matrix may be, for example, a network of interwoven fibers such as paper, cotton swab, nylon or polyester mesh, or felt. Thus, the absorbent materials utilized in this invention, for example, for absorbing fluids to provide a flow through a sample collection surface are porous matrices or materials.

In the context of entrapment of complexes of target material and dye and the removal of unbound dye, the term "wash" or "washing" refers to a fluid transport of sufficient unbound dye to enhance the detection of complexes. It is understood that, in many cases, excess washing of dyed materials can remove bound dye in addition to unbound dye. Therefore, when implemented the washing is not so extensive that removal of bound dye interferes with the detection of the presence of target material using detection of the presence of dye retained in or on a solid support or matrix.

In certain embodiments, the sample collection matrix is an absorbent material, e.g., an absorbent pad, or the surface of an absorbent pad. In certain embodiments, the sample collection matrix binds the target material, in others the sample collection matrix entraps precipitated target material or the surface of the matrix retains dye/target material complexes.

In yet other embodiments, the device is arranged such that the sample collection matrix of the sampler is washed by wash solution by diffusion, which may be assisted by physical agitation. Generally in such embodiments, the sampler would then be removed from the dye-bearing wash solution. The target material, e.g., protein, would be bound to, entrapped by, or otherwise immobilized on or in a portion of, the sampler.

By "entrapment" or "entrap" is meant a physical association, which may be chemical, electrostatic or steric in nature, such that a target material is retained in a matrix even in the presence of forces that otherwise might have a tendency to remove such target away from the matrix. This can occur, for example, through precipitation of target material such that the material becomes insoluble, e.g., using precipitating dyes such as Ponceau-S. In this way, washes may be performed to separate small, unreacted or unbound dye molecules from larger, dye/target material complexes, thus facilitating testing of samples.

The term "precipitate" or "precipitation" as used in the specification and claims includes the usual understanding of precipitation as a settling or deposition of solid particles out of solution. Additionally, the term as used herein also includes any general retention of solid or particulate matter, by any force, within, or in some cases on, an absorbent collection pad matrix or sampler or other solid phase surface. Thus, the definition includes but is not limited to target matter coming out of solution, target material agglutination, and target material conformational changes that act to obstruct the exit of these materials out of a matrix by creating complexes or other physical structures which cannot readily move through the pores of the porous material. Thus, those skilled in the art will readily be able to select appropriate materials and conditions for precipitation or other entrapment of a particular target material/dye combination, e.g., selection of a porous material with an appropriate average pore size which will allow target material to penetrate into the porous material, but small enough to prevent dye/target material complexes from quickly being transported out of the porous material or binding of indicator dye to the matrix (e.g., absorbent pad or suitable covering membrane).

In embodiments making use of a target material precipitating dye, e.g., protein precipitating dye, the dye stains/colors and immobilizes target material, e.g., a protein (e.g., protein adsorbed to or precipitated on an absorbent swab or pad). In this context, "immobilizes" means that the target material is removed from or prevented from entering the bulk of a solution (e.g., a dye solution or wash solution), such as by precipitation of the target material/dye complex, entrapment of the target material and/or target material/dye complex, or attachment of the target material to an insoluble or solid material, e.g., a particle, matrix, or support. In embodiments where target material binds to a matrix or surface, a precipitating dye need not actually precipitate a target material as it is immobilized by the binding to the solid matrix or support.

Certain of the embodiments described below demonstrate that the scope of the invention may also contemplate some minimum manipulation of device components and devices in which the device does not remain sealed after sample insertion and/or in which separate manipulation of one or more device components is needed. Thus, the device in one embodiment includes a sampler for collecting a target material or contaminant, a signal generator for providing a target material binding dye, a sampler washer for washing unbound dye away from dye which is bound to target material and/or wetting agent reservoir, and at least one housing to contain the signal generator and sampler washer and/or wetting reagents.

In certain embodiments, the sampler may take the form of a wand, wick, stick or any other configuration that is suitable for taking up a particular type of sample. Such a sampler wand is generally an absorbent stick, preferably flattened, with a sample collection pad or surface on a terminal portion of the stick. The stick may also have an absorbent material in communication with the sample collection pad/ membrane, e.g., on the other side of the same end of the stick, with communication through a hole or holes in the stick. Thus, in these configurations, there is an absorbent pad or is material which is, or is adapted to be, juxtaposed to the collection surface for drawing target material and/or dye and/or wash solutions across the target material, e.g., a protein contaminating a surface, and can facilitate entrapment of this target material on or within the pad matrix. The device incorporates a sampler washer to wash unbound dye from the sampler collection pad or preferably a wetting agent reservoir, preferably into an absorbent pad or reservoir, which in some embodiments, such as the wand, is juxtaposed to or integral with the sampler collection pad/ membrane, and in others is an elongated extension of the sampler collection pad or an abutting absorbent material housed by a sampler stick or housing and providing for a flow of wash solution across the sample. Optionally, the device further includes both a wetting agent or solution and sander washer wherein the wetting agent can be utilized to wet the sample collection matrix or surface. Such wetting can assist in sample collection and/or in picking up a quantity of dry dye. A wetting solution can be the same or different from the wash solution. Thus, in applications where a moistened sample collection matrix is desired, the sample collection surface or matrix can be pre-moistened or can be moistened using a wetting solution.

As indicated above, in particular embodiments, a sampler wand may be constructed either with a sample collection pad/membrane but no additional absorbent material, or with both a sample collection pad and an absorbent material for drawing fluids through the sample collection pad, e.g., with a sample collection pad on one side in communication with an absorbent pad on the other side. Generally a sampler wand has a handle, preferably made of a non-porous material such as various plastics, coated papers, glass, or metal. Preferably the handle is at least one inch long, and more preferably 2, 4, 6, or 8 inches long. In other embodiments, such as ones including a sampler stick, there is no sandwich of the type described above. Rather, the body or housing of the sampler is hollow or integral with an internal reservoir adjacent or connected to the sample collection surface for receiving or flushing the dyed sample of unbound dye with washing solution, or for providing a wetting agent to the membrane.

Thus, the term "sampler stick" refers to an elongated housing structure which includes a sample collection surface, pad or membrane, and at least one reservoir. For example, a sampler stick may contain a wash solution, and/or a wetting agent, along with a sample collection pad. The wetting agent or wash solution may be in continuous communication with the collection pad or may be separated with a separator until communication is desired. Alternatively, a sampler stick can contain a reservoir with dry absorbent material for absorbing wash and/or wetting solution in communication with the sample collection surface. Exemplary sample sticks are shown in FIGS. 9–12.

In certain embodiments, the device includes a housing with a plurality of reservoirs, e.g., three reservoirs containing wetting agent, dye (dry or in solution), and wash solution. After taking up a sample and a quantity of dye, the sample collection surface of the sampler is merely pressed against a wash solution reservoir to flush unbound dye from the sample, as the sampler itself unlike the embodiments above, possesses a complementary receiving reservoir. The sampler stick formats, exhibited herein, are illustrative, but not limiting. As an alternative, the reservoir in the sampler stick can contain wetting/wash solution, and, following sample and dye uptake, the sample collection surface is pressed against an absorbent material in a housing to cause a flow of wash solution across the sample.

Figure 3:
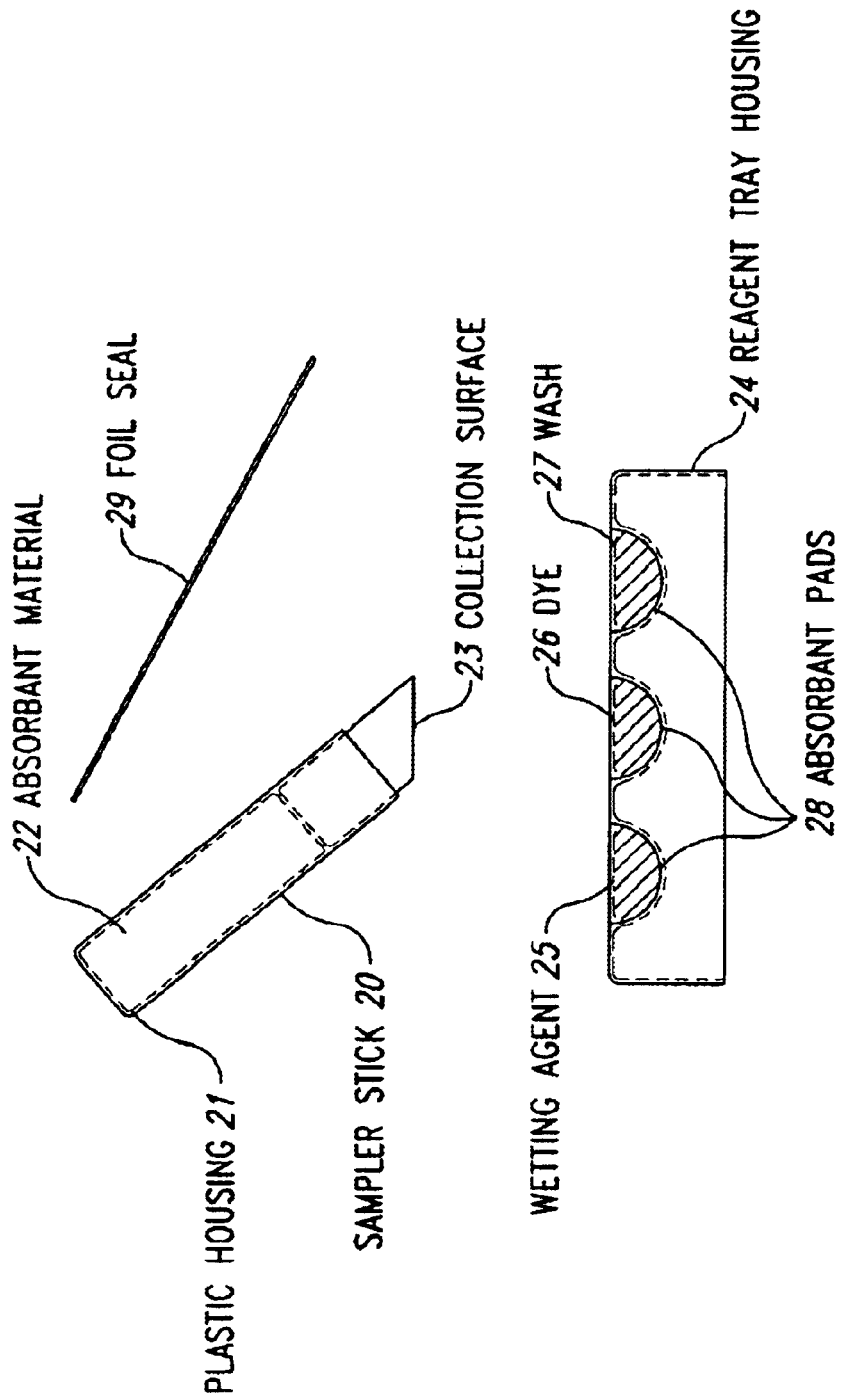
FIG. 3 illustrates an embodiment in the published art containing a sampler stick and a reagent dish with three wells; one with sampler wetting solution, one with dye, and one with wash solution.
Figure 4:
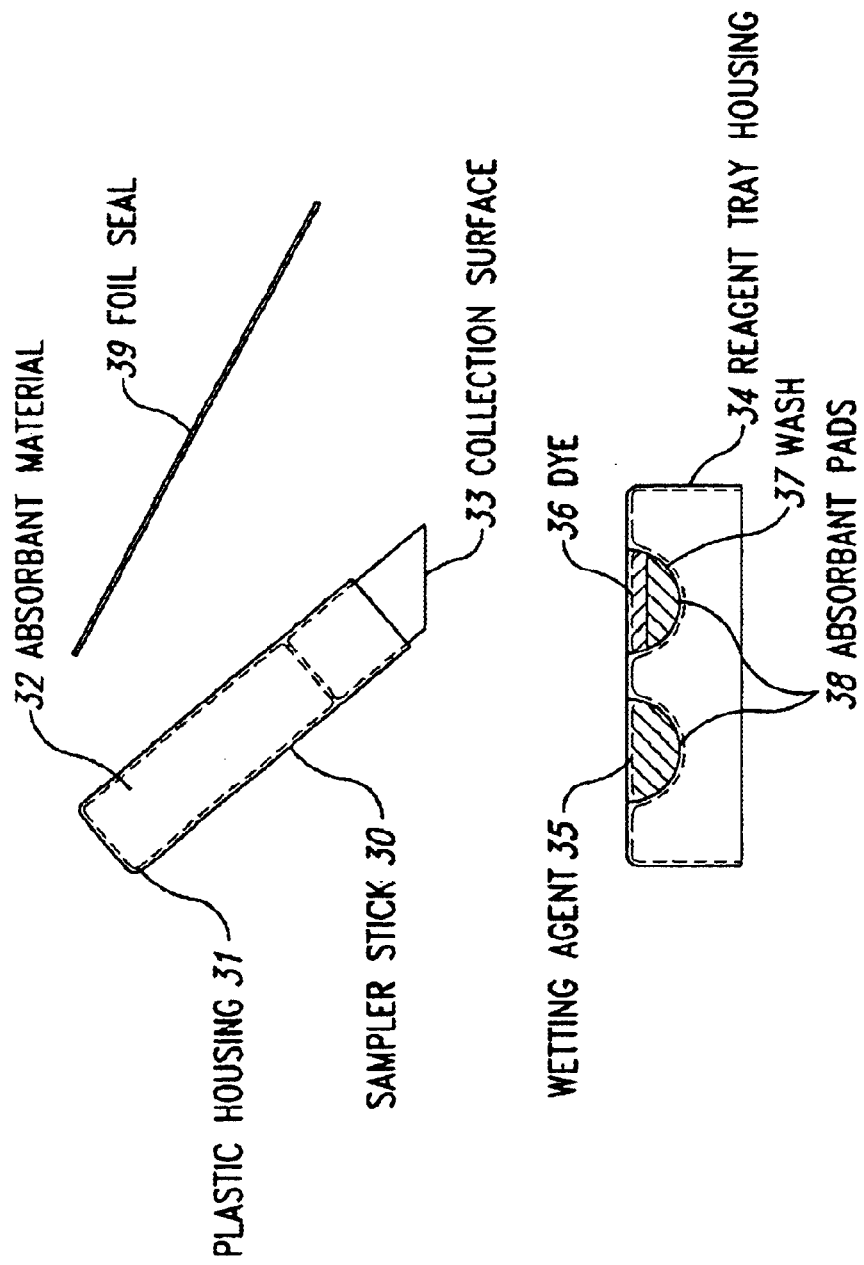
FIG. 4 illustrates another embodiment to that of FIG. 3 where the reagent tray is simplified to two wells with the dye and wash reagents present in the same well separated by an impermeable but rupturable membrane.
Figure 5:
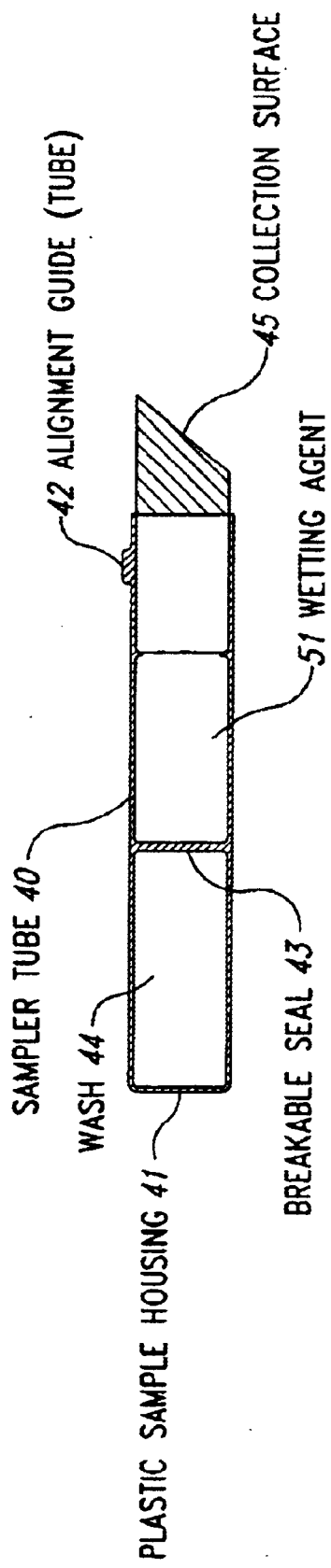
FIG. 5 illustrates an embodiment of a device in the published art where the wash solution is contained in a sampler stick separated from the sampling surface by an impermeable membrane. Prior to use, the sample collection end of the sampler stick sealably engages with a cavity in a housing. The dye is present in the same cavity and separated from the wash surface by a permeable membrane. The opposite end of the housing contains an absorbent material and can be sealably engaged with the collection end of the sampler stick following sample collection.

Such sampler sticks can utilize a housing containing reservoirs in a planar arrangement, e.g., as shown in FIGS. 3 and 4, or can use a housing in the form of a cap (e.g., FIG. 5). For example, such a cap can be reversible, such that in one orientation the cap seals and/or protects the sample collection surface. In the opposite orientation, the cap provides contact with dye and wash solution. Those skilled in the art will recognize that a variety of arrangements can be used to provide moistening of the sample collection surface, dye uptake or transport onto or into the sample collection surface and matrix, a source of wash solution, and a complementary absorbent material to receive wash solution as it washes the sample of unbound dye.

In some embodiments, certain of the reservoirs and/or reagents are contiguous or adjacent but separated by rupturable membranes or separators that, when broken, permit the flow of reagents across a collected/exposed sample to effectively wash the sample or wet the sample collection surface. FIG. 9 is exemplary but not limiting.

Some embodiments make use of solid dye which is hydrated and presented to a sample in response to a physical stimulation such as a rupturing of a membrane or membranes which maintain the dye in a dried, segregated state. FIG. 4 is illustrative, although by no means intended to be limiting. (The combined dye/wash solution reservoir in FIG. 4 could contain dry dye or a dye solution.) For example, a moistened sample collection surface can be touched to a dry dye such that a quantity of dye is transferred to the sample collection surface. The dye can contact target material directly and/or by fluid transport through a porous matrix to contact target material within the porous matrix.

The foregoing embodiments preferably utilize the properties of precipitating dyes but provide surprisingly good results with certain classes of frequency shift dyes. As illustrated by those embodiments, the invention also provides methods of using such dyes to fix or retard the egress of target materials, e.g., protein, from porous matrices into which target material has already been introduced, e.g. by swabbing. Thus, the introduction of target material as contemplated by the instant invention is not facilitated by or dependent on movement of particles or molecules in an electric field. Likewise, the method does not utilize a separation of components of a sample due to differential migration within the porous matrix. Instead, the matrix need merely be compatible in size to allow the initial ingress or association of target with matrix, and the influence of dye acts to thwart or inhibit the target material from leaving the matrix. This may be due, for example, to precipitation, conformational changes, agglutination, or any other result of dye binding which has the effect of sufficiently immobilizing target material in the porous matrix that unbound dye can be washed away and dyed target material visualized in the matrix. Alternatively, the immobilization can be due to chemical or electrostatic binding of target material to matrix. Further, matrix constituency is irrelevant as long as the criteria described above are met and as long as the dye is otherwise compatible with, or can be made compatible with, the matrices, e.g with neutralizing agent.

Illustrative but not limiting of the possible materials that may be used for the porous matrices are those discussed below under the definition of "sampler". The dye should not bind to the matrix material to such an extent that dye bound to target material in the matrix cannot be distinguished from dye binding to matrix.

In accord with the aspects above, the immobilization or entrapment of target materials with a solid matrix, e.g., in a porous matrix, provides a method for detecting the presence of target material in a sample. As previously indicated, the method involves entrapping or otherwise immobilizing target material/precipitating dye or frequency shift dye complexes on or within a solid matrix. For example, such complexes can be entrapped in a porous matrix by binding of target material with precipitating dye or by collection of dye/target material complexes on or in a collection surface or porous matrix. Generally, when using precipitating dyes the method includes washing away unbound dye to allow convenient visualization or other detection, e.g., detection using an instrument such as a spectrophotometer or fluorometer. When using frequency shift dyes only wetting sample collection and visualization is required. The method can involve various matrix materials, neutralizing agents, wash solutions and/or wetting solutions, and dyes as described herein for other aspects.

For the methods herein involving precipitating dyes, azo dyes, preferably diazo dyes, which preferably have at least one, and preferably a plurality of sulfonic acid groups, e.g., 2, 3, or 4 groups (which may be prepared in the corresponding salt form) are preferred. The red dye, Ponceau-S, Sigma Chemical Co., St. Louis, Mo. (chemical abstracts service registry number 6226-79-5, (3-hydroxy-4-[2-sulfo-4-(4-sulfophenylazo) phenylazo]-2,7-naphthalenedisulfonic acid, tetrasodium salt], $HOC_{10}H_4(N=NC_6H_3(SO_3Na)(N=NC_6H_4SO_3Na))(SO_3Na)_2$, F.W. 760.58) is exemplary. Ponceau-S is soluble in water, slightly soluble in ethanol, and insoluble in vegetable oils. It is stable at room temperature in acetic acid and in preferred embodiments is used to stain proteinaceous matter using a dye concentration of about 0.1–1.0% (w/v) in about 1–5% (w/v) acetic acid. The stain may be quickly removed upon addition of 0.1 N NaOH, or by excess wash solution. The terms "azo dye" and "diazo dye" have the meanings as generally accepted in the dye industry. The term "sulfonated" in connection with the dye compounds refers to the presence of sulfonic acid substituent groups. Such groups may be present in a corresponding salt form.

Advantageously, Ponceau-S binds rapidly to proteins and precipitates or immobilizes them in addition to staining/coloring them. Thus, such a precipitating dye is generally used to bind to and precipitate target material, e.g., protein, in or on a solid matrix. In such case, unbound dye is generally washed away from dye/protein complexes, providing visual detection of sample protein. In such embodiments the dye does not bind to the solid matrix to such an extent or under such conditions as to prevent or interfere with detection of dye/protein complex.

The invention provides a method for detecting protein on a solid surface. Preferably the method is applied in testing for contamination on to surface, e.g., food processing residue. The method involves contacting a solid surface, e.g. a metal surface, with a Ponceau S dye solution under conditions in which Ponceau S dye binds to protein. The rapid binding of Ponceau S to protein allows sufficient dye to bind to protein even on vertical surfaces. Preferably the method allows immediate visualization of protein-bound dye on the surface without further processing. If desired, the method can further include washing the surface with a wash solution which can wash away unbound dye. Preferably the dye is used at a concentration of 0.1–1.0% in dilute acetic acid. The dye solution and/or a wash solution can further contain neutralizing agent as described above.

In certain other embodiments of the present invention, the binding of dye to target material is detectable by a color change of the dye or dye solution, e.g., by a frequency shift of the dye on binding (color change) to target or of a dye solution by dye depletion. Preferably a self-contained sampling/testing device incorporates a frequency shift dye. Frequency shift dyes have their absorption or reflection or emission changed on interaction with target material, thereby differentiating bound from unbound dye. Such dyes can allow convenient detection of target material even without separation of bound and unbound dye, thus not requiring a wash solution.

Therefore, in certain embodiments, the sample wash is able to transport sample material, e.g., target material from the collection portion or surface of the sampler. Device embodiments wherein liquid-phase analysis is performed typically employ a reading portion of the device that permits the sample reaction to be visualized or analyzed, with or without the aid of an instrument such as a spectrophotometer. The sample material is washed into the reading portion or alternatively carried into the reading portion on the sampler.

In certain other embodiments employing frequency shift dyes or other dyes where a change in dye color is to be detected, the sampler may be contained within a lower housing that provides protection for the sampler from pre-testing contamination.

Additionally, an upper housing may sealably engage the lower housing such that the two housings are in communication during the test. The sampler is preferably fixed to the upper housing. Within or comprising such housings may be a chamber or reservoir to hold a wash or a wetting solution or a combined sample wetting signal generator or separate reservoirs to hold each of a signal generator and a wetting solution. A chamber may further include a breakable shaft contiguous with the chamber that, upon breakage, exposes an orifice through which the contained solution may flow to the sampler and may further flow to a read portion for evaluation. Thus, the wetting solution can flow through a hollow shaft in a swab in the device, flow through the swab tip to the target collection pad/membrane/surface.

Frequency shift dyes provide convenient detection of bound dye even in the presence of unbound dye when the frequency shift is large enough to distinguish the two. In cases where an instrument is to be used to read the binding results, the frequency shift can generally be smaller than if a visual reading is to be utilized. For machine reading, preferably an absorption shift on binding (expressed as a wavelength shift) is at least 20 nm, more preferably at least 50 nm, still more preferably at least 75 nm, and most preferably at least 100 nm. For visual reading, preferably an absorption frequency shift on binding is at least 50 nm, more preferably at least 75 nm, still more preferably at least 100 nm, and most preferably at least 120 nm. For example, an absorption peak of COOMASSIE blue stain under acidic conditions shifts from about 465 mn to about 595 nm on binding of the dye to protein. For a visual reading it is preferable if the absorbance change produces a color change rather than just a shade change. For example, the GELCODE® reagent changes from amber to blue on protein binding. A fluorescent emission shift is preferably at least 20 nm, more preferably at least 40 nm, still more preferably at least 75 nm, and most preferably at least 100 nm.

GELCODE® includes colloidal COOMASSIE® G-250 dye. Colloidal COOMASSIE® blue dyes may also be formed as described in the art. For example, in Neuhoff, et al., *Electrophoresis* 6:427–448 (1985) and in Neuhoff, et al., *Electrophoresis* 9:255–262 (1988). In general, these solutions utilize COOMASSIE blue dye® in an acidic aqueous solution with ammonium sulfate or ammonium iron sulfate. In one example, the solution contains 0.1% weight/volume (w/v) COOMASSIE blue G-250 in 2% w/v phosphoric acid, and 6% w/v sulfate. In an alternative solution, the dye contains 10% w/v ammonium sulfate and 20% w/v methanol. Preferably, the pH of the solution is between 1 and 2 and the ammonium sulfate or ammonium iron sulfate concentration is between 2% and 15% more preferably between 4 and 10%, and most preferably between 5 and 8% w/v. The pH should not be so low that the dye molecules are rapidly degraded and the ammonium sulfate concentration should be selected so that the solution takes on a color characteristic or the colloidal form, preferably the majority of the dye molecules are present as colloidal particles rather than being in free solution or precipitating out of solution.

Another class of frequency shift dyes has been referred to as "protein error" dyes in the literature. The shift in the observed absorption peak upon binding proteins is believed to be due to a shift in pKa of an ionizable group or groups on the dye. This family includes but is not limited to the triphenyl methane dyes, such as bromophenol blue, bromocresol green, and tetrabromophenol blue. In one embodiment utilizing this class of dyes, the present invention concerns a self-contained device having a sampler for collecting a sample which may contain a target material, and a signal generator having a contactable dye that binds to the collected target material. In this embodiment the dye is bound either covalently or non covalently at or near the surface of the sampler (FIGS. 9–12). The dye could be either bound directly to the absorbent material or bound to a membrane which covers all or part of the sampler surface as in FIGS. (9–11). The membrane should have several characteristics in order to be useful in this application. Firstly, it should either bind the dye directly through non covalent forces or posses a structure which allows modification to accept covalent attachment of a dye. Secondly, the membrane should be somewhat porous, allowing passage of excess wetting agent and other solutes through to the absorbent material. Thirdly, since it is in contact with the surface to be tested for protein, it must be resistant to excessive fraying. Examples of such materials include, but are not limited to, nylon, rayon, others polyesters, cellulose nitrate, and cellulose acetate.

For example, a nylon membrane is briefly exposed to a buffered solution of bromophenol blue at 5–500 µg/mL, preferably at 50–300 µg/mL, most preferably at 150–250 µg/mL. Although a preferred formulation of this buffer is 0.8 M NaCl, 0.1 M sodium citrate, 0.04 M acetic acid, 4.3% (v/v) ethanol (pH 2.2), this is not limiting. An alternative formulation of the buffer is 0.4 M NaCl, 0.1M citric acid, 4%ethanol (pH 2.2). The membrane is then rinsed in a low pH buffer to retain its yellow color and then it is dried and stored desiccated at room temperature. Under these coating and storage conditions the attachment of the dye to the membrane is stable. The dye-containing membrane is then placed at sampler collection surface and is in communication with or can be placed in communication with an absorbent material able to take up liquid from a wetting agent. The device may be constructed with any of many possible structural configurations, depending on the requirements of the particular application, e.g., depending on the specific type of dye used and the type of target material to be tested.

The device may but need not also contain a wetting agent. In one such embodiment, the wetting agent is contained in a separate compartment of the device (FIG. 9). Alternatively the wetting agent may be stored in a separate housing of the device, access to which is gained by puncturing or removing a seal (FIG. 10). The wetting solution may be contained in an ampoule which is contained in the housing. In addition, certain embodiments of the invention employ a pre moistened sampler such as that depicted in FIG. 11. The wetting agent serves one or more of several purposes including: (1) It may contain agents which facilitate the release of the target material from the surface of the material to be tested; (2) It may contain neutralizing agents which neutralize or partially neutralize the deleterious effects of interfering materials; and (3) It will be of such a composition as to facilitate the frequency shift of the dye in the presence of target material. In embodiments using these dyes the target (e.g., protein-containing) solution is presented to the dye at a pH value just below that causing the color change. For bromophenol blue, the wetting solution should preferably be buffered at pH 1.5–2.4, most preferably at pH 2.2+/−0.2, and contain a detergent or detergents to solubilize the target, and a neutralizing agent or agents as described below. A preferred , but not limiting formulation of such a wetting solution is 0.1 M NaCl, 0.5 M citric acid, 4.5 mM potassium sulfite, 3 mM sodium thiosulfate, 0.4% sodium dodecyl sulfate, and 0.5% tergitol (pH 2.2).

As appreciated by one of ordinary skill in the art, certain device embodiments will accommodate the use of various types of target material binding dyes, e.g., precipitating dyes or frequency shift dyes. For example, embodiments which utilize a wash to carry sample material away from a sampler can be but need not be utilized with a frequency shift dye. Such devices can also be used with a precipitating dye where there is the capability to wash unbound dye away from target material bound dye in or on the sampler or on a porous separator. In accord with certain embodiments described herein which incorporate a wash solution in a reservoir in a sampler portion or upper housing, sample can be collected on a sampler, contacted with dye, e.g., from a reservoir in the sampler portion or upper housing or by dye contained in the sampler prior to sample collection, and then washed by a wash solution contained in a reservoir in the sampler portion or upper housing. Preferably in such embodiments, the collection surface of the sampler is pre-moistened.

Similarly, a device in which a dye solution is in a reservoir contactable with a sample collection surface (see e.g., FIG. 2 below) can be used with a frequency shift dye or with a precipitating dye. With either type dye, sample material is transferred to contact the dye on the sampler. For a frequency shift dye, dye binding to target material is detected by a color change of the dye as dye binds target material in the dye solution or on the sampler, or as dye is depleted from the solution as dye binds to target material in or on the sampler.

The terms "sampling/testing device" or "self-contained sampling/testing device" indicate that the device is constructed so that all components for a particular assay are provided within a single device along with a means for introducing a sample into the device. It may, however, be advantageous for certain embodiments to utilize a separate apparatus for incubation during the assay or for reading results of the assay.

By "sampler" is meant a device component (or components) which allows one to obtain all of or a portion of a sample which may be present on a surface, in a solution or in an atmosphere to be tested. For example, the sampler may be an absorbent pad, an absorbent pad which has a dye-containing membrane fixed to its surface, or a swab with a shaft and an absorbent tip. The shaft of the sampler or the sampler stick housing may be hollow, and may further include a vent. As alternatives, the sampler/swab may take the form of a Q-Tip® or a simple pad. The swab may include natural or synthetic materials so long as deposition of a sample there to may occur and dye binding to the swab does not interfere with detection of the target substance so as to prevent such detection. The absence or reduction of such interference may be provided, for example, by selection of material and/or by the physical interrelationships of device components. The material may be but is not limited to sponge, mylar, nylon, dacron, rayon, porex, porous polypropylene, porous polyethylene, glass fibers, paper, or various other woven or felted fibers such as nitrocellulose, cotton, wool, cellulose, or combinations thereof. In a preferred embodiment in which the swab includes a shaft, the swab shaft is preferably hollow, allowing the sample wash and/or dye solution to flush the collected sample material from the swab into a reaction and/or read chamber or allowing a wetting solution to moisten the sampler. The swab may be provided for use in a pre-moistened form to assist in solubilizing and absorbing sample material into the sampler, or can be readily moistened from a reservoir within the device containing a wetting solution, e.g., in a saturated absorbent matrix. The moistening fluid may be a buffer, water, acid, or base depending on the type of dye used. Those skilled in the art understand the selection of a compatible moistening fluid for the dye and target material involved in a particular type of test. The sampler may function through capillary action, for example a capillary tube or tubes. The sampler may comprise a pipetting means. The sampler may comprise a chamber that captures a sample of an atmosphere, such as the atmosphere present in an enclosed work space. The sampler may assume virtually any shape or combination of shapes, e.g., planar, elongated, rectangular, circular, elliptical, cylindrical, spherical, cubical, conical, etc. Preferably the sampler is designed to enable a user to conveniently reach into locations in equipment, such as food processing or hospital equipment, which are difficult to access. Thus, the sampler is preferably constructed to provide an extension with a thin cross-section, e.g., a cross-sectional area of less than 2 in$^2$, more preferably less than 1 in$^2$, and in certain embodiments less than ½ in$^2$. Such extension is preferably least 2 inches in length, preferably least 4, 6, or 8 inches in length. Such extension may be provided, for example, by a wand handle, a swab shaft, or an elongated housing, or combinations thereof.

The term "sampler portion" refers to a structural assembly which includes a sampler and also includes additional components which allow the sampler to be sealed or attached to the remainder of the device, and may also include one or more reagent spaces, such as a reservoir for a sample wash solution.

By "sampler washer" is meant a device component (or components) which allows the removal of all or a part of a sample present on the "sampler". For example, in some embodiments an upper housing or sampler portion or sampler stick comprises a chamber as a reservoir containing a fluid in which the fluid may be selectively released as desired, ordinarily to release a sample that has been obtained or to wash unbound dye away from dye/target material complexes. In an alternative embodiment, the upper housing or sampler portion may contain a container such as, but not limited to, an ampoule or a packet. The ampoule or packet may contain a fluid as described above, which may be selectively released. In an alternative embodiment the upper housing or sampler portion may contain two containers, both or either comprising, for example but not limited to, an ampoule or packet containing the same or different fluids or dry substances. In another embodiment a fluid may be directly contained in the upper housing or sampler portion and a container or containers containing a fluid or dry substance (or more than one fluid or dry substance) be contained therein. In yet other alternatives, the lower portion of the housing or the lower housing may contain a fluid that is used to wash the sample from the sampler, for example, by inserting the end of the sampler into the fluid or otherwise forcing the fluid against or through the sampler.

By "wash solution" is meant a solution, e.g., an aqueous solution, capable of separating unbound dye from dye/target material complexes and/or carrying sample materials from a sampler to another location. The solution may also serve the function of a wetting agent, e.g., for moistening a swab or collection surface in anticipation of or facilitation of a sample collection. A wash solution for use with a particular dye does not contain such amount of agents which tend to disrupt binding of that dye to target material that determination of target material binding is prevented. Preferably no such agents are present, but in some cases it may be desirable to include a low level of such an agent or agents, for example, to minimize binding of dye to a porous matrix, thereby enhancing contrast and improving target material detection. Those skilled in the art will readily be able to select an appropriate wash solution for a particular dye. In embodiments utilizing Ponceau S. dye, the wash solution and/or wetting agent are preferably dilute acetic acid solutions, preferably with 0.1 to 10% acetic acid in water, more preferably 0.5 to 5%, still more preferably 1 to 5% acetic acid.

By "wetting agent" is meant an aqueous solution capable of moistening the sampler and/or hydrating dye to facilitate detection. In this context, the wetting agent does not remove unbound dye and thus is not a wash solution.

By "signal generator" is meant a chemical compound or physical stimulus or biological agent that provokes a measurable or discernable response in the presence of a target material; by chemical compound is meant a chemical dye, an enzyme, or other organic or inorganic structure capable of inducing such response.

The term "target material binding dye" or "dye" refers to a compound which will preferentially bind to a target material in a sample as compared to binding to other molecules which are likely to be present in such samples. Thus, the dye may bind to other molecules at a level equal to or greater than that for binding to the target material, but such other molecules are ones which do not cause the characteristic change in property upon binding said molecule (e.g., frequency shift) and/or are generally not present in samples to be tested, such as samples to be tested in evaluating process contamination. The preferential binding need not occur under all conditions, but at least occurs under the assay conditions selected for use in the device of the present invention. The dye compound also is detectable using visual or spectroscopic means, and preferably absorbs or fluoresces at visible wavelengths so as to give a characteristic color. Binding of the dye to target material, e.g., protein, preferably results in a color change and/or precipitation of the protein that is visible. Thus, for example, the term "protein-binding dye" refers to a compound that preferentially binds to protein, polypeptides, or oligopeptides in preference to other molecules. The dye, while active in aqueous form may be initially dry and hydrated during the testing process, e.g., when contacted with wetting/washing solution.

By "frequency shift dye" is meant a composition which upon interaction with the substance to be detected exhibits a characteristic, detectable change in the light emission or absorption spectrum of the dye molecule. Preferably the alteration of the light absorption characteristics of the dye molecule is observed. Changes in absorption or emission spectra can include, for example, the appearance or increase of absorbance or emission peaks or bands, the disappearance or reduction of absorbance peaks or bands and combinations of these. The frequency shift dye may be a protein binding dye that is colloidal such as Coomassie® blue dye, preferably GelCode® Blue Stain Reagent Pierce Chemicals, Rockford, Ill., a "protein error dye" such as bromophenol blue, or other dyes whose spectra change in the presence of target.

The term "colloidal dye" refers to a dye which is in a finely divided state in a liquid, such that the solid particles of dye are in the range of 1 to 1000 nm, preferably in the range of 1–100 nm, and more preferably in the range of 5–100 nm. This does not mean that all of the dye present in the liquid is in the form of such particles, as those skilled in the art recognize that the colloidal form is generally in thermodynamic equilibrium with solubilized dye and/or with solid dye particles larger than colloid size, e.g., larger than 1000 nm. Most useful are colloidal dyes where the amount of dye in colloidal form is sufficient to alter the color of the dye solution as compared to solutions containing the same amount of dye but in which the dye is in solution and/or in non-colloidal particles. In certain embodiments, at least 30% of the dye molecules are in colloid size particles, preferably at least 50%, and more preferably at least 70% or 90%. As recognized by those skilled in the art, a transition from soluble form to colloidal form of a molecule in liquid solution can be monitored by an increase in light scattering of the solution.

In embodiments employing a frequency shift dye of the protein error dye family the wetting and or wash solutions are buffered at a pH near that at which the color change occurs. For bromophenol blue, the wetting and/or wash solution (if present) are preferably buffered near pH 2. At and below this pH the dye is yellow and with increasing pH the dye changes to blue/green. In the presence of protein the color change occurs at an anomalous pH. Thus, when bound to protein, bromophenol blue is blue/green rather than yellow at pH values near 2.0. A reasonable explanation for this "protein error" is that binding of the dye decreases the pKa of a group or groups whose ionization determines the absorption spectrum of the dye, thereby causing the color change to occur at an anomalously low pH value.

The term "swab" as used in the claims is used as a noun to denote an absorbent and/or adhesive pad that serves to collect sample target material in prelude to or concurrent with exposure to a signal generator, i.e., a dye.

By "neutralizing agent" is meant a chemical compound or solution that helps to neutralize potentially interfering compounds present on the surface being tested or in a wetting agent present in or on a sampler collection surface, which compounds may interfere with the dye binding to the target material, e.g., protein. Exemplary neutralizing agents include sodium thiosulfate, sodium sulfite, sodium meta bisulfite, Tween-20, (Polysorbate 20) sodium sulfate, sodium dodecylsulfate, tergitol (now called NiaProof Type 4), $MgCl_2$, and Triton-X® (Octoxynols; α-[4-(1,1,3,3,-Tetramethylbutyl)phenyl-ω-hydroxypoly(oxy-1,2-ethanediyl; polyethylene glycol P-1,1,3,3-tetramethylbutylphenyl ether). All are available from Sigma, St. Louis, Mo. Triton-X® can be used preferably at an effective concentration of about 0.01–0.5% weight volume. Sodium thiosulfate may be used, preferably at an effective concentration of about 0.01–1.0 mg/mL. $MgCl_2$ is preferably used at a concentration of 0.2–20 mg/mL. These neutralizing agents may be incorporated into any, all, or a combination of the wetting, wash, dye, or sample solutions provided. One of skill in the art will recognize that other neutralizing agents may be substituted provided they do not significantly interfere with the signal generator mechanism and measurement, and will understand what neutralizing agents are appropriate for a particular application or can determine whether or not a potential compound is appropriate by simple testing.

Thus, by "neutralize" is meant to inactivate potentially interfering compounds present on the sample surface without significantly disrupting the signal generator's function in combination with the target material and the rest of the device.

By "effective concentration" is meant one that supplies, in whole or in part, the intended or desired effect e.g., the desired neutralizing effect.

The term "participates" as used in the claims denotes an assistance in the movement and/or gathering of target material onto the sampler, for instance by premoistening of an absorbent collection swab or pad.

By "reading portion" is meant a distinct section of the device housing wherein a reading or measurement or detection may be taken.

The term "in succession" connotes a temporal order but does not preclude the use of wash solution as a wetting agent for a sampler swab in prelude to exposure to dye. Thus, the wash solution may be used twice, both before and after the dye.

The terms "contacted with", "contacted by" or "on contact with" denotes the direct or indirect touching of one object with another. Certain embodiments have the contact mediated through a pierceable membrane, which is rupturable by the sampler to effect the dyeing and washing of a target material presented on the sampler.

The term "segregates" as used herein denotes a separation and/or containment which may be undone upon proper stimulation, for example the piercing of a membrane by a sampler to allow mixing of components from each side of the membrane.

By "stably packaged" is meant that the dye or other signal generating component may be stored prior to use for prolonged periods of time, for example, a year or more if stored at 4° C., and still provide a signal upon activation. In one embodiment of the invention the signal generating means, e.g., comprising a colloidal dye solution, is stably packaged within a sealed glass ampoule. The ampoule may be a borosilicate glass, for example Pyrex®. It may be an "onion-skin" type of glass ampoule. In other embodiments, a signal generating component, e.g., a dye, is sealed within a chamber by a membrane or membranes.

As understood by those skilled in the art, the stability of a dye molecule will depend on the storage conditions, thus, the storage form can be varied as appropriate for a particular dye. If the dye is sufficiently stable in the test solution, the dye solution can be packaged in the device as a single solution. Alternatively, if the dye is not sufficiently stable in the assay solution, the stability can be enhanced by packaging the dye within the device separated from one or more other components of the test solution until mixing is desired. Thus, for example, the dye and/or components decreasing dye stability can be separated within the device by any of a variety of methods, such as by using separate reservoirs or capsules or ampoules or separators or combinations thereof, such that one or more can be ruptured, broken, or opened to allow mixing of various components at a desired time or times.

By "separator" is meant a device component(s) or structure for separating two portions of the device, e.g., for separating the region containing the sampler from the region in which detection is performed until introduction of the sample into the detection region (read portion) is desired or for separating a sample on the sampler from a dye solution until contact between the sample and the dye is desired. For example, a separator may be a porous plastic or hydrophobic material filter, however, the porosity is not such that the sample would filter through without the application of a force, other than gravity, on the sample. As further examples, the separator may be a one-way valve, or a puncturable membrane or a breakable or rupturable reservoir or capsule or ampoule.

A "reservoir" may be a well, ampoule, recess, void, or chamber capable of holding a liquid or solid. Such reservoir may be encased or contained by a rigid, soft, or flexible housing such as a plastic. A reservoir may be or include an absorbent pad that is saturated or capable of absorbing solution or solutions, e.g., target material, dye, wash, wetting agent, or combinations thereof. Such absorbent material is preferably located in a depression, void, chamber, cavity or the like of a housing.

Preferably the dye and test conditions are selected such that a readable result is provided within one hour at room temperature, more preferably within 30 minutes or 20 minutes, still more preferably within 10 minutes or 5 minutes, and most preferably within less than 1 minute. Such rapid results are particularly advantageous for field sanitation testing, restaurant food preparation areas, hospital operating room, physicians' or veterinarians' offices and examining rooms, and laboratory hygiene monitoring as retention of the samples for long periods of time is not required and stability or consistency of the read of the completed test is enhanced.

As indicated above, a particularly advantageous embodiment of the present invention is adapted for protein detection, and therefore provides for the rapid and convenient testing of surfaces or solutions for contamination by protein-containing substances. The presence of protein can be a good indicator of residual food contamination remaining after cleaning procedures have been completed, as protein is a component of many food products. For example, in one application, the device will allow for testing of surfaces in food production plants, supermarkets and restaurants to ensure that cleanup procedures after food processing have been effective. In other applications, the device would ensure that appropriate cleaning of testing equipment or surfaces in hospital or veterinary operating rooms, examining rooms, or laboratory surfaces after patient work-up or specimen testing was performed.

Certain embodiments utilize a dye capable of precipitating as well as staining protein, for example, Ponceau-S. Ponceau-S is particularly useful due to its speed of staining as well as its ability to both precipitate and stain protein. Other embodiments utilize frequency shift dyes such as bromophenol which rapidly change color in the presence of target. Yet other embodiments are slower and utilize colloidal protein binding dyes via a single step, integrated sampling assay device with visually distinct color changes in the presence of small amounts of protein material, e.g. colloidal Coomassie® blue such as found in GelCode® Blue Stain Reagent. Colloidal Coomassie Blue imparts a convenient spectral or color shift in the presence of protein.

By "protein" is meant peptide polymers (i.e., polymers of amino acids) and thus includes oligopeptides, full-length cellularly-produced polypeptides, degraded cellular polypeptides, complexes of polypeptides, and polypeptides associated with other molecules.

In certain embodiments, the results of a test using the device can be read visually. In other embodiments, the result can be read in an instrument, such as a spectrophotometer, fluorimeter, or colorimeter. These devices are most useful for applications employing frequency shift dyes.

The device in one embodiment includes a sampler and a combined sample treatment, sample wash and signal generator stably packaged, preferably allowing easy visual interpretation.

By "a combined sample treatment, sample wash and signal generator" is meant components or structures to contain a target material binding dye, which preferably either precipitates and stains proteins, or else creates a frequency shift on contacting protein, e.g., colloidal dyes, protein error dyes. In either case, the dye is bound to the sampler or the dye solution can be released at will to wash a sample on or from the sampler thereby signaling the presence, absence, or quantity of protein present. In preferred embodiments the solution collects in a reading portion of the device. The dye solution or wetting agent can also treat the sample in a desired manner, for example, by solubilizing or permeabilizing cell walls and/or membranes of microorganisms (e.g., bacteria and fungi) or other cells.

By "fix" is meant that target material in the presence of a precipitating dye, e.g. Ponceau-S, is relatively slowed or halted from diffusing from or otherwise exiting the porous matrix in which it has entered or is contained, as compared with target material/matrix in the absence of dye.

Other specific applications of the invention include but are not limited to the following: the testing of surfaces for other types of contamination such as carbohydrates, lipids and microorganisms; the testing of liquid solutions for the presence of proteins, carbohydrates, lipids and microorganisms; the testing of air or gas for proteins, carbohydrates, lipids and microorganisms; and the testing of other materials such as dirt, vegetable material, manufactured articles, spices, powders, chemicals, debris and other types of samples familiar to those skilled in the art for such contaminants as protein, carbohydrates, lipids, nucleic acids, microorganisms, toxins, poisons, byproducts, adulterants and other materials recognized by those skilled in the art and capable of binding to dyes or ligands capable of being contained in colloidal or other forms which sequester or contain such reagents so that reaction with specific target materials results in or can be stimulated to result in rapid, detectable and distinct changes.

In accord with the provision of sampling/testing devices as described above, in another aspect, the invention provides a method of making such a test device by depositing a target material binding dye, preferably a precipitating-type dye or a frequency shift dye within a reservoir in a self-contained sampling/testing device or upon or within surface to be contacted by the sample (e.g., membrane, pad, etc.).

As indicated above, for device embodiments which include a sampler portion and a housing, the dye solution may be deposited in a reservoir in the sampler portion or alternatively in the housing. In embodiments in which the device includes an upper housing and a lower housing, the reservoir may be in the upper housing or alternatively in the lower housing. The dye used is preferably a precipitating dye, such as Ponceau-S. Alternatively, a frequency shift dye such as the protein error dye, bromphenol blue, or a colloidal dye such as colloidal Coomassie® blue is used which exhibit frequency and color shift change an contact with protein.

In another aspect, the invention provides a method for detecting the presence of a substance, i.e., a target material, by using a sampling/testing device as described above. Thus, in this embodiment, the method involves obtaining a sample which may contain the substance to be detected (i.e., the target material) on or in the sampler. Depending on the type of sample, this may, for example, involve swabbing a surface, depositing a solubilizing or suspension liquid on a surface and then taking up at least a portion of that liquid, or taking up a sample of liquid from a bulk liquid, such as by pipetting or in a capillary tube or by moistening an absorbent material. The sample is contacted with a target material binding dye, e.g., a precipitating dye or a frequency shift dye, as described above within the device, and the presence of the target material in the sample is determined by detecting the occurrence of a dye color change, e.g., a dye frequency shift, by observing a visually detectable change in the color or shade of the dye solution following contact with the sample or by reading a change or changes in an absorbance or emission spectrum of the dye in a reading instrument following contact with the sample or by detecting the presence of bound dye on or in a matrix which immobilizes dye/target material complexes but which allows unbound dye to be separated, e.g., by washing away.

In particular, a method of sanitation testing is provided in which a device as described above is used to detect the presence of contaminants on or from a surface or in solutions, such as following cleaning procedures on a surface. In particular embodiments, the method involves contaminant testing of surfaces or solutions in food processing facilities such as a food production plants, restaurant, hospitals, laboratories, physicians' offices, ambulances, or veterinary hospitals. In preferred embodiments, the contaminant to be detected is protein residue.

The devices of the present invention generally are constructed such that a sample to be tested can be obtained on or in a sampler. The device is constructed so that any remaining steps involved in detecting the presence of a target material in the sample can be carried out following placement of the sample-bearing sampler within the housing without further addition of assay components. This description generally describes embodiments which include a precipitating or frequency shift dye, but applies also to the use of target material binding dyes generally.

Thus, the device components are arranged so that the sample, or at least a sufficient portion of the sample to allow detection of the presence of target material, is contacted with a dye. The mixture is present in, or is transferred to, a portion of the device where the results can be read, e.g., visually or in a spectrophotometer, a fluorometer, or other reading instrument. Specific embodiments are described below and in the figures with device elements arranged in particular ways. However, it is clear that the invention also concerns devices with elements selected and arranged in other ways to accomplish the above process. Thus, for example, the dye solution can be located such that it is used as the wash solution to carry sample from the sampler to the reaction reading portion, the sample can be directly delivered into the dye solution (e.g., by pipetting a liquid sample into the dye solution or by inserting the sample-bearing portion of the sampler into the dye solution), or a wash solution can carry sample from the sampler into the dye solution. In view of the description herein, those skilled in the art will understand how the specifically described embodiments can be altered to provide each of these and other formats.

Figure 8:
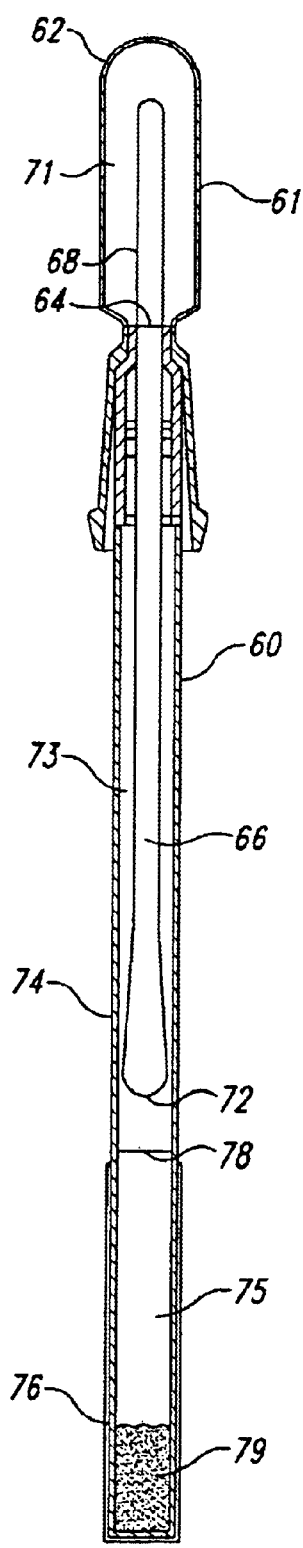
FIG. 8 shows an embodiment in the published art of a device in which the upper portion of device contains a sampler and a sampler wash solution which contains no dye.

Embodiments described in FIGS. 1–5 are particularly adapted for use with precipitating dyes, embodiments described in FIGS. 6–8 are particularly adapted for use with frequency shift dyes such as colloidal Coomassie blue., and embodiments described in FIGS. 9–12 are particularly adapted for the use of frequency shift dyes of the "protein error" type, such as bromophenol blue.

Figure 1:
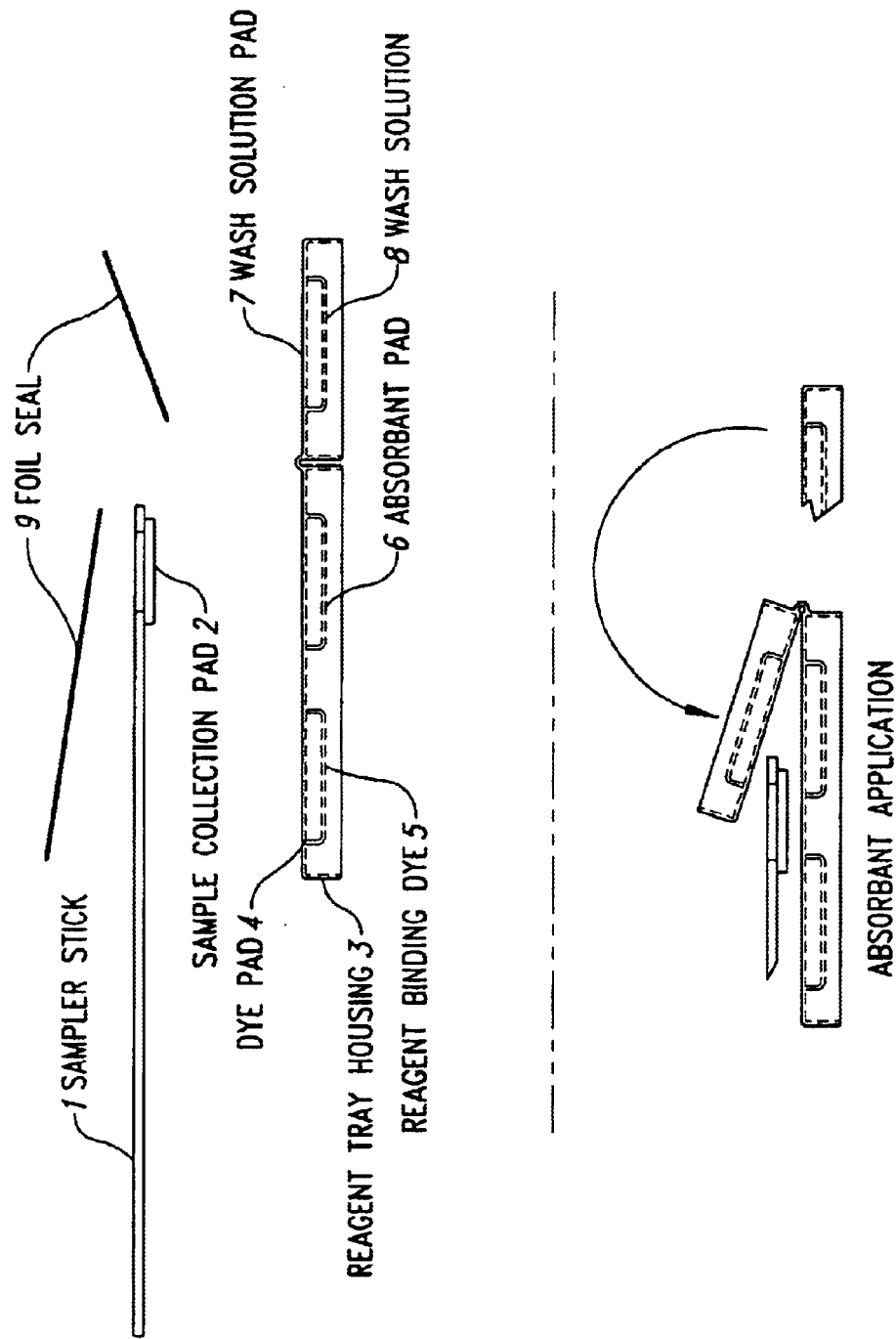
FIG. 1 illustrates an embodiment in the published art containing a sampler wand with an absorbent sample collection pad, and a foldable book encompassing reservoir pads for dye, absorbent and wash solution.

Referring to FIG. 1: the device includes a plastic housing (3) with three wells. One well contains the target binding dye (5) and an absorbent dye pad (4). The second well contains only an absorbent pad (6). The third well, separated from the other two by a hinge, contains an absorbent pad (1) and wash solution(s). The housing (3) is covered by a foil seal (9) that is removed prior to use. A separate sampler wand (1) incorporates a sample collection pad (2). The sample collection pad (2) is moistened by contacting it with the wash solution pad (7). The sampler wand (1) is then used to swab a sample surface, e.g., a food contact sample surface, removing and absorbing food residue into the sample collection pad (2). The sampler wand (2) is placed into the device housing (3) and contacted with the dye pad (4) for a few seconds to transfer dye (5) to the sample collection pad (2). The sampler wand (1) is then placed on the absorbent pad (6) and the wash solution pad (7) pressed against the backside of the sample collection pad (2). Pressure is maintained for several seconds allowing wash to be drawn through the sample collection pad (2) into the absorbent pad (6), removing unbound dye. The sample collection pad (2) is ten observed for the presence of color on its surface. The presence of colored dye is indicative of the presence of target binding material. In this embodiment, the sample collection pad is selected such that target material will remain immobilized on and/or in the pad matrix during a washing step.

Figure 2:
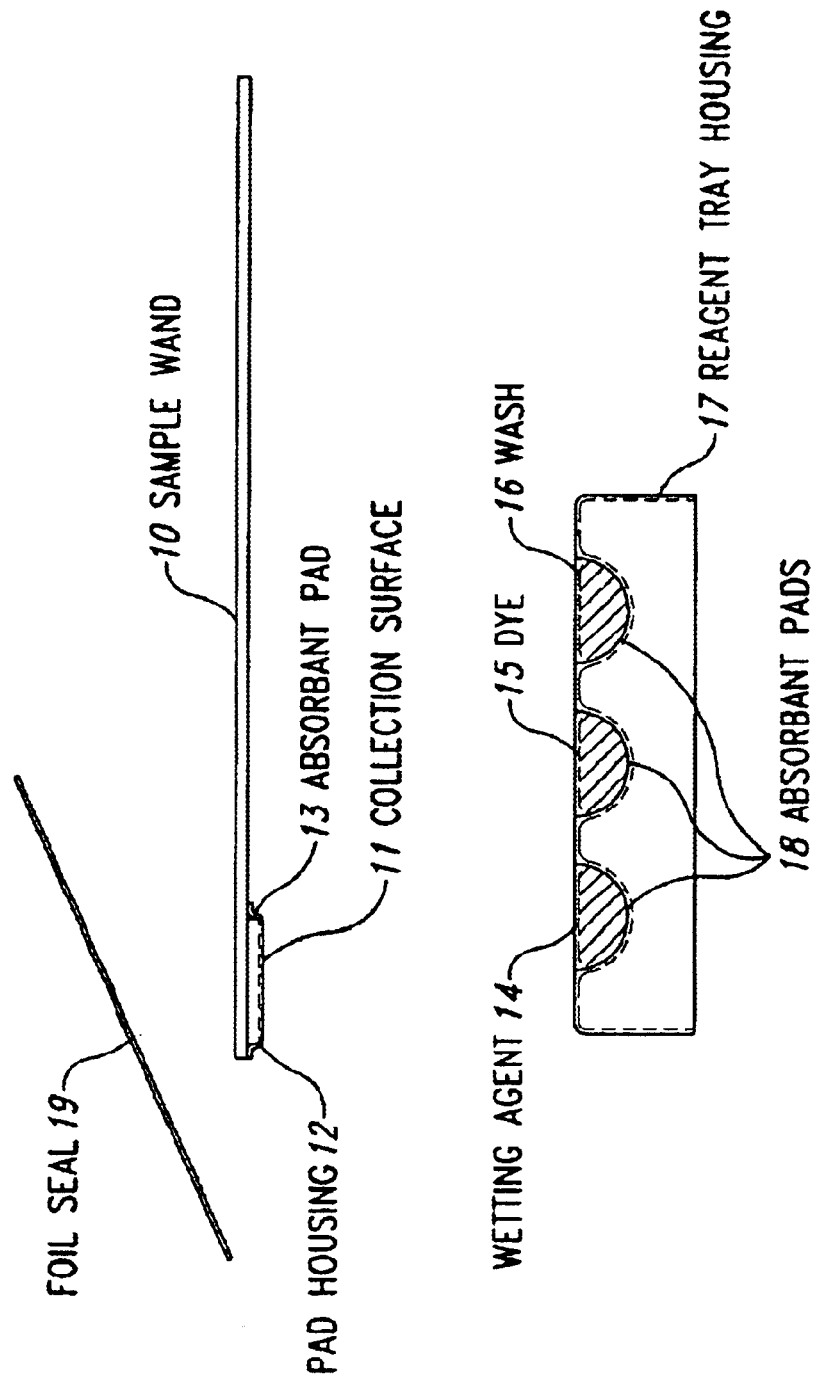
FIG. 2 illustrates an embodiment in the published art containing a sampler wand with a sample collection pad and an absorbent backing, and a reagent dish with three wells: one with swab wetting solution, one with dye, and one with washing solution.

Referring to FIG. 2: The device includes a sampler wand (I) and a series of three reservoirs in a housing/reagent tray (17). One reservoir contains wetting or washing agent/solution (14) used to moisten the sample wand before swabbing the surface. The second reservoir contains the dye reagent (15). The third reservoir contains a wash agent/solution that may or may not be identical to the wetting/washing agent (16). The reagents are localized in absorbent pads (18) at the bottom of the individual well/reservoirs. The reagent tray (17) is covered by a foil seal (19) that is removed prior to use. The sample wand (10) comprises a collection surface (11) that abuts an absorbent pad (3) and the two pieces are held in place by a pad housing (12). The test is performed by moistening the collection surface (11) of the sampler/wand (10) in the wetting/washing agent (14). The surface to be tested is then swabbed and the sample on the collection surface (11) is then contacted with the dye (15) and then the excess dye is washed away when the surface is subsequently placed into the wash well (16). In each case the dye and wash agents are moved to/through the collection surface by absorption into absorbent padding or material (13).

Referring to FIG. 3: The reagent device is essentially the same as in FIG. 2; however, the sampler (20) is in the form of a stick instead of a wand, wherein the collection pad (23) surface may be distinct from but contiguous with an absorbent material (22) encased by a stick housing (21). Alternatively, the absorbent collection pad (23) material extends down into the housing (21) and provides an absorptive draw. Otherwise, this embodiment is manipulated in the same manner for wetting of the collection surface, treating the sample with the dye, and using the wash reagent to wash away excess dye as in FIG. 2.

Referring to FIG. 4: The device uses the sampler stick as FIG. 3, but has the reagent housing (34) with 2 instead of 3 wells. The first well contains the wetting reagent (35) that is used for moistening the collection pad (33) surface, and the second well has two compartments vertically arranged, with the dye (36) layered on top of the wash (37). The dye is present in dry form on top of a breakable membrane (36a). Following contact with the dye, the membrane (36a) is pierced with the sampler stick and wash solution (37) is absorbed into and through the collection pad (33).

Referring to FIG. 5: This device is an embodiment that has the reagents in the reagent tray/housing (46) that is in the shape and function of a cap, as well as inside the sampler stick (40). The reagent tray/housing (46) in this embodiment fits onto the end of the sampler stick (40) as a reversible cap. The collection pad surface (45) is pre-moistened with wetting agent (51). In the exemplary form, the collection pad surface (45) is covered by the end of the reagent tube housing (46) with a breakable membrane (47) protecting the collection surface (45) from the dye (48) in an absorbent pad (49). The sample stick (40) is removed from the reagent tube housing (46) and used to collect the sample. The reagent tube housing (46) is then put back on the sampler stick (40) after being rotated 180 degrees and the same side of the cap is placed on the sampler stick employing the alignment guide (42). The collection pad surface (46) pierces an initial barrier (47), thereby coming into contact with dye (48) and taking a quantity of that dye on the collection surface (45). Then the sampler stick (40) is put onto the other end of the cap at which point the breakable seal (43) in the sampler stick housing (41) is broken, allowing the wash reagent (44) in the sampler stick (40) to migrate through the collection pad (45) surface and into the absorbent material (50) in the cap/reagent tray housing (46).

This effectively washes away excess dye, so that only the dye remaining of the collection surface is dye which has been immobilized due to binding to target material, e.g., protein.

Referring to FIG. 6: This embodiment of the device (60) includes a sampler portion or upper housing (61) a dye reservoir (62) containing the target binding dye (70); an orifice (64) communicating with the hollow swab shaft (66), exposed by breaking off the snap plug (68); a housing (74); an absorbent swab tip (72); and a lower read chamber or read portion (76).

Referring to FIG. 7: In another embodiment the device includes an upper housing (80), an upper barrier means (81) between the upper housing (80) and the upper section (82) of a lower housing (87). The upper housing (80) and upper barrier means (81) define a chamber (88). A sampler (83) is attached to the upper housing. The lower portion of the lower housing (87) forms a read portion (85).

Referring to FIG. 8: This embodiment is as in FIG. 6, except that the dye reservoir (62), contains a wash solution (71) which does not contain a dye. The housing contains a foil barrier (78) (i.e., a separator) dividing the housing into an upper section (73) and a lower section (75). The lower section contains a dry dye (79), and forms a sealing, slidable junction with the upper section (73). In this embodiment, other types of barriers can be used to prevent the wash solution from washing the sampler before such washing is desired. Similarly, other types of separators can be used to divide the housing into upper and lower sections. Also, the dye in the lower section can be a dye solution or suspension rather than a dry dye. The slidable junction between the upper and lower sections of the housing may include a threaded surface(s) such that the upper and lower sections may be screwed together, thereby piercing the separator with the sampler.

Referring to FIG. 9: This embodiment is as in FIG. 4, except that the dye is bound, either covalently or non covalently to a membrane (89) which is in communication with the absorbent material (90) on the collection surface of the sampler (91). The membrane and absorbent material are inserted into a plastic housing (92). Together these components form the sampling stick (93). In this embodiment a reagent tray housing (94) is employed. This tray contains an absorbent pad (95) containing wetting agent (96).

Referring to FIG. 10: This embodiment is as in FIG. 9 in that the dye-membrane (97) is in communication with the absorbent material (98) on the collection surface (99) of the sampler tube (100). In this embodiment the wetting solution (101) is contained within a sealed compartment in the plastic sample housing (102) and is separated from the absorbent material and thus the dye-membrane by a breakable seal (103).

Referring to FIG. 11: This embodiment is as in FIG. 10 in that the dye-membrane (104) is in communication with the absorbent material (105) on the collection surface (106) of the sampler tube (107). In this embodiment the wetting solution (108) is contained within a breakable ampoule (109) within a sealed compartment in the plastic sample housing (110).

Referring to FIG. 12: This embodiment is as in FIGS. 9–11 in that the dye-membrane (111) is in communication with the absorbent material (112) on the collection surface (113) of the sampler tube (114). In this embodiment the wetting solution (115) is used to pre-moisten the absorbent material (112) and thus the dye-membrane (111). To prevent evaporation of the wetting solution (115), the sampler tube or sampler tubes are sealed within an air-tight pouch (116).

In addition to the embodiments described in the figures, additional embodiments can be constructed with various combinations and arrangements of elements which also accomplish contacting a sample with a target material binding dye, e.g., a precipitating or frequency shift dye, within the self-contained sampling testing device. Exemplary selections and arrangements are described. In accord with the embodiments described above, a device may be constricted to include a sampler portion which sealably attaches to a housing, or may be constructed as an upper and a lower housing in which the sampler is attached to the upper housing and the upper and lower housing sealably engage. Other variants can also be constructed.

As previously indicated, in the various embodiments different types of samplers can be utilized. These include, for example, swabs, pipettes and capillaries. For embodiments in which the sampler is a swab or other wiping device, a sample washer is provided. In certain embodiments, the sample washer includes a reservoir containing a wash solution that can be used to wash the sample from the sampler. Delivery of the wash solution to the sampler can be accomplished in a variety of ways including, for example, rupture of a membrane to allow wash solution top through a hollow sampler shaft, or breaking the tip or plug to expose an orifice communicating with a hollow sampler shaft allowing the fluid to flow down the shaft, or rupture of a packet or ampoule thereby releasing a fluid that can then flow down a sampler shaft to wash the sample.

The wash or wetting solutions may also be constituted and packaged in a variety of different ways as appropriate for various configurations and dye selections. For example, as described above, the wash solution may include the dye. However, in certain embodiments it may be preferable to package the dye separately from the wash solution. For example, the dye and other wash solution components may be separated in the upper reservoir until mixing is desired. As an example, a concentrated dye solution may be provided in a breakable ampoule or rupturable packet within a reservoir chamber containing other wash solution components. Alternatively the dye and other wash solution components may be in separate chambers separated by a separator. Breakage of the dye container or combining the contents of separate chambers, then results in mixing and thus provides a combined dye wash solution. Such an arrangement may be desirable, for example, where the dye molecules would not have long-term stability in the presence of one or more other wash solution components. Alternatively, the wash solution and dye may be separated by providing the wash solution only in the upper reservoir and providing the dye in a reservoir or ampoule or packet or chamber in a lower portion of the device, e.g, in a lower portion of the housing or lower housing.

In embodiments where the sampler is a pipette or a capillary the sample can be removed from the sampler in a variety of ways, such as by expelling the liquid sample with air, or by washing the sample from the pipette or capillary with a wash solution. In general, to remove the sample, the upper portion of the device will be deformable to allow a creation of pressure to push the liquid sample from the pipette or capillary.

Similar to the embodiment described above in which the dye is separated from other solution components in the sampler portion of upper housing, in embodiments where the dye is contained in a lower portion of the device the dye can be separated from other solution components by placing either or both of the dye or other components into separate chambers, ampoules, packets, or other structures such that the components can be mixed at a desired time.

In yet another embodiment, the sampler is directly inserted into a solution in a lower portion of the device. For example, in certain embodiments the upper portion of the device does not contain a reservoir with a wash solution. Instead, the wash solution with or without dye is contained in a lower portion of the device and the sampler is inserted into the wash solution following sample collection. In such embodiments the wash solution can be separated from upper portions of the device by a barrier, for example, a rupturable membrane or one-way valve or deformable constriction through which the sampler can be inserted. Also, in such embodiments, as noted, the dye may be packaged separately from the wash solution or may be incorporated in the wash solution. As described before, such separation may be accomplished by the use of separate chambers, rupturable packets, breakable ampoules, rupturable membranes, semi-porous filters, and other such structures.

The method of using one embodiment of the device to test for the presence of protein will be briefly described. This embodiment of the device has the structure of the device illustrated in FIG. 9, and utilizes a dye bound to a membrane at the surface of the sampler to detect the presence of protein on a surface.

A sampler stick (93), stored in a plastic container or sealable pouch with desiccant is removed and the top of the reagent tray housing (94) is removed exposing the absorbent pad (95) containing wetting agent (96). The collection surface (91)/dye membrane (89) is briefly pressed against the absorbent pad (95) activating the device. An area (2 in×2 in) to be tested for protein is swabbed with a moistened collection surface (91), allowing a portion of the protein material bind to the dye on the dye-membrane (89). The sampler (61) is then sealably engaged onto the housing (74). If protein is present in the sample the dye on the dye-membrane (89) will change from a yellow color to blue within 1 minute. If no protein is present the color of the dye-membrane (89) will remain yellow.

The device embodiments described herein are constructed from any of a variety of materials or material combinations, including but not limited to plastics. Injection mold castings or any other means for generating suitable device housings may be employed. In appropriate devices, well/reservoirs may be machine-drilled or injection molded or formed by other methods suitable for forming such cavities in the particular materials. Those skilled in the art are familiar and can select suitable materials and construction techniques. Also where appropriate, as in embodiments such as the book of FIG. 1, separate housings and pieces may be joined by hinges, snaps, latches, Velcro®, or any other connector that does not impede the ability of the reagents to function. The absorbent swabs and collection surface materials, already described, are comprised of any of the following illustrative materials or functional equivalents thereof: sponge, mylar, nylon, dacron, rayon, porex, porous polypropylene, porous polyethylene, glass fibers, paper, or various other woven or felted fibers such as nitrocellulose, cotton, wool, cellulose, or combinations thereof. These may in turn be attached to housings where appropriate, such as in the embodiments of FIGS. 1,2, or 3, by glue, adhesive, or any other means which does not interfere with target material collection, staining or, in the case of precipitating dye use, the precipitation or other immobilization of target material.

Those skilled in the art will recognize that this and other embodiments of the present invention can be used in a variety of ways, including the following:

(1) Testing of liquid samples to determine if they contain contaminating material. The procedure utilized to test for material in a liquid sample would be similar to the procedure used to test a surface, with the difference being that the sample tested is a liquid.

(2) Testing of any sample for contamination and using an instrument read instead of a visual read.

EXAMPLES

Although the following examples are patterned after applications to the food industry, similar results would be obtained regardless of the source of protein (e.g., human or animal sera or other secretions, etc.

Example 1

Exemplary devices were constructed as generally described in FIG. 2 and used with a precipitating dye (Ponceau 5) and a frequency shift dye (a colloidal Coomassie Blue dye, Gelcode®) and used to test food surfaces soiled with milk, cheese, roast beef, turkey, or tomato. The surfaces were also tested with a food industry-accepted means of measuring surface contamination based on ATP detection (LIGHTNING, produced by IDEXX Laboratories, Westbrook, Me.)(used according to manufacturer's instructions) as well as the protein detection devices described for this invention. As indicated, two different embodiments of the present invention were used. One with Ponceau-S as the protein-binding dye, and one with Gelcode®—a colloidal Coomassie blue dye.

Stainless steel surfaces were smeared with the indicated food materials. For each test, a sample was obtained from the surface by swabbing with the moistened sampler collection surface of a sampler from the particular device. "Dirty" indicates that the surface was tested following application of the food residue, to the surface; "wiped clean" indicates that the surface was wiped free of visible food residue with a dry paper towel; and "scrubbed clean" indicates that the surface was wet cleaned with a brush and detergent type cleaning solution in a manner commonly used for cleaning in the food processing industry.

For the Ponceau S device, the absorbent pad of the sampler was moistened with the wetting agent, a sample was swabbed from the surface, then the absorbent pad of the sampler was touched briefly (a few seconds) against the dye. The absorbent pad of the sampler was then dipped in the wash solution to wash away unbound dye.

The Gelcode® device was used similarly except that the color change of the dye was observable both in the dye solution and on the sampler pad.

The results are shown in Table 1. The data indicate tat to device is able to distinguish the three different states of the surfaces (dirty, wiped clean, and the more thorough, scrubbed clean) for each food type. Both dyes gave results that allow the test operator to distinguish between dirty, minimally cleaned (wiped) and thoroughly cleaned (scrubbed) surfaces. Results for the LIGHTNING® device range from 0–7.5. Dye results are read by eye and assigned a numeric value from 0–5. In both cases the higher the number, the greater the indicated level of contamination.

TABLE 1

Comparison of Bioluminescence assay (Lightning) to protein detection devices. Lightning results in zones (0–7.5). Dye results are read by eye and assigned a numeric value from 0–5.

|  | Milk | Cheese | Roast Beef | Turkey | Tomato |
|---|---|---|---|---|---|
| Bioluminescence |  |  |  |  |  |
| Lightning dirty | 3.3 | 2.55 | 4.9 | 5 | 6.05 |
| wiped clean | 2.4 | 2.1 | 3.45 | 3 | 4.85 |
| scrubbed clean | 2.05 | 1.65 | 1.65 | 2.05 | 2.35 |
| Protein Detection Devices |  |  |  |  |  |
| Ponceau S dirty | 3.5 | 4.5 | 4 | 3 | 1.5 |
| wiped clean | 125 | 1.25 | 0.75 | 0.25 | 0.25 |
| scrubbed clean | 0 | 0 | 0 | 0 | 0 |
| Gelcode dirty | 4.5 | 4 | 5 | 4 | 3 |
| wiped clean | 3.5 | 2.5 | 225 | 1.5 | 0.75 |
| scrubbed clean | 025 | 0 | 0 | 025 | 0.5 |

Example 2

An exemplary device constructed as generally described in FIG. 6 and containing 2 ml Pierce Gelcode® dye was used in a test to determine detection sensitivity of the device. Presence of protein was detected using qualitative visual reading and by reading the optical density (OD) at 595 nm, with the reported OD being the mean of two readings.

Bovine serum albumin (BSA) at various concentrations was dried on clean 4"x4' stainless steel coupons. For each sample tested, the pre-moistened swab portion of a device was swiped over the coupon surface with firm pressure to collect the sample. The swab was inserted into the housing, and the dye reservoir bulb snapped to the side to deliver the dye into the lower read chamber. A visual interpretation is then made, followed by transfer from the read chamber to a disposable cuvette for reading at 595 nm. The results are shown in Table 2.

| Sample | O.D. | Visual Interpretation |
|---|---|---|
| Negative control (PBS) | 0.0006 | Negative |
| BSA, 5 µg/test | 3.3800 | + + + + |
| BSA, 50 µg/test | 1.3570 | + + + |
| BSA, 10 µg/test | 0.4130 | + + |
| BSA, 5 µg/test | 0.1930 | + |
| BSA, 2.5 µg/test | 0.0900 | + |

BSA refers to Bovine Serum Albumin.

The results demonstrate that this embodiment of the device has a detection sensitivity of about 2.5 µg protein/test.

Example 3

An exemplary device as in Example 2 was used in a comparison test of biological contamination with the Konica Hygiene Monitoring Kit. The Konica kit was utilized according to manufacturer's instructions with reading after 10 minutes at room temperature. The exemplary device was utilized as follows.

Various different sources of protein were dried upon clean 4~x4~ stainless steel coupons, which had been marked to divide each coupon into two equal parts. The exemplary device was used to collect the sample from the left side of the coupon surface. Following the Konica kit procedure, the corresponding right side of the coupon was sampled with the Konica swab. Visual interpretation for the exemplary device was made immediately upon activation. The Konica test was read at 10 minutes according to kit instructions. The stainless steel coupons were then washed with a mild detergent (Palmolive®) and water, and after drying, each side of the coupon was retested to detect any remaining contamination on the surface.

The results of the comparison test are shown in Table 3. Cleanliness levels for the Konica kit are shown according to a cleanliness standard where:

Level I (Clean)

Level 2 (Less Clean)

Level 3 (Slightly Dirty)

Level 4 (Dirty)

TABLE 3

| Sample | Konica Kit | Exemplary Device |
|---|---|---|
| Milk on coupon | Level 3–3.5 (slightly dirty) | + + + + |
| 1 wash | Level 1–1.5 (clean) | + + + |
| 2 washes | Level 1 (clean) | Negative |
| 5 µg/test BSA standard | Level 1 (clean) | +/− |
| 1 wash | Level I (clean) | Negative |
| 1:400 Plasma | Level 1 (clean) | + + |
| 1 wash | Level 1 (clean) | Negative |

The results indicate that the device is more sensitive than the Konica test system, in addition to the advantages of being faster and more convenient to we.

Example 4

An exemplary device as described in FIG. 9 was used in a comparison test of biological contamination with the Konica Hygiene Monitoring Kit (AssureSwab).

The exemplary device was prepared as described in the text using a nylon membrane which had been treated with a 200 µg/mL solution of dye. The sampler surface was briefly exposed to wetting solution and the test area (4 inx4 in) immediately swabbed. A transition from a yellow color to blue-green occurred within one minute if protein were present. The intensity of the blue-green color was assessed on an arbitrary scale from 0 (yellow) to 2 (deep blue-green).

The Konica kit was utilized according to manufacturer's instructions with reading after 10 minutes at room temperature.

Various different sources of the test protein BSA (bovine serum albumin) were dried upon clean 4 inx4 in sections of a plastic plate. The exemplary device was used to collect the sample from one section of the surface. Following the Konica kit procedure, the section was sampled with the Konica swab. Visual interpretation for the exemplary device was made immediately upon activation. The Konica test was read at 10 minutes according to kit instructions.

The results of the comparison test are shown in Table 4. Cleanliness levels for the Konica kit are shown according to a cleanliness standard where:

Level I (Clean)

Level 2 (Less Clean)

Level 3 (Slightly Dirty)
Level 4 (Dirty)

TABLE 4

| Sample | Konica Kit | Exemplary Device |
| --- | --- | --- |
| 10 μg BSA | Level 1 (clean) | 0.1 |
| 25 μg BSA | Level 1 (clean) | 0.3 |
| 50 μg BSA | Level 1+ (clean) | 0.3 |
| 100 μg/BSA | Level 2 (less clean) | 1.0 |

The results indicate that the device is more sensitive than the Konica test system, in addition to the advantages of being faster and more convenient to we.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The solutions, dyes, and methods described herein as presently representative of preferred embodiments, arc exemplary, and are not intended as limitations on the scope of the invention. Changes therein and other uses will occur to those skilled in The art which are encompassed within the spirit of the invention as defined by the scope of the claims.

It will be readily apparent to one skilled in the art that varying substitutions and modifications may be made to the invention disclosed herein without departing from the scope and spirit of the invention. For example, those skilled in the art will recognize that the invention may be practiced using a variety of different dyes, and pH buffers, as well as additional reaction components.

The invention illustratively described herein suitably may be practiced in the absence of any element or elements, limitation or limitations which is not specifically disclosed herein.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

What is claimed is:

1. A self-contained sampling/testing device comprising:
 a. a sampler for collecting target material from a sample; and
 b. a signal generator comprising a dye which binds to said target material to signal the presence of said target material,
 wherein said sampler contains an absorbent an at the surface of which is positioned a membrane to which the dye is attached either covalently or non covalently.

2. A self-contained sampling/testing device comprising:
 a. a sampler for collecting target material from a sample; and
 b. a signal generator comprising a dye which binds to said target material to signal the presence of said target material,
 wherein said sampler contains an absorbent pad which has the dye attached directly to its surface either covalently or non covalently.

3. The device of claim 1 or 2, wherein said dye is a protein binding dye.

4. The device of claim 1 or 2, wherein said target material is protein.

5. The device of claim 1 or 2, further comprising a separate reagent housing containing an absorbent material and a wetting/neutralizing solution.

6. The device of claim 1 or 2, wherein said absorbent pad is pre moistened with wetting/neutralizing solution.

7. The device of claim 6, wherein said wetting/neutralizing solution comprises a neutralizing agent to neutralize any compounds in the sample that might interfere with the binding of said dye to said target material.

8. The device of claim 7, wherein said neutralizing agent is selected from the group consisting of sodium thiosulfate, $MgCl_2$, sodium dodecyl sulfate, tergitol, polyethylene glycol P-1,1,3,3-tetramethylbutylphenyl ether, and polysorbate 20.

9. The device of claim 1 or 2, wherein said dye is a frequency shift dye of the protein error family.

10. The device of claim 9, wherein said dye is bromophenol blue.

11. A self-contained sampling/testing device comprising:
 (a) a sampler for collecting biological target material from a sample; and
 (b) a signal generator comprising a frequency shift dye of the protein error family, wherein said dye binds to said biological target material and produces a color change upon binding to said target material, unbound frequency shift dye need not be separated from biological target bound frequency shift dye in order to detect the presence of target material, and
 wherein said sampler contains an absorbent pad at the surface of which is positioned a membrane to which the dye is attached either covalently or non covalently.

12. The device of claim 11, further comprising a separate reagent housing containing a wetting agent.

13. The device of claim 11, wherein said dye is bromophenol blue.

14. The device of claim 11, further comprising a separate reagent housing containing a wetting solution, said solution comprising a neutralizing agent selected from the group consisting of sodium thiosulfate, $MgCl_2$, sodium dodecyl sulfate, tergitol, polyethylene glycol P-1,1,3,3-tetramethylbutylphenyl ether, and polysorbate 20.

* * * * *

UNITED STATES PATENT AND TRADEMARK OFFICE
CERTIFICATE OF CORRECTION

PATENT NO. : 6,863,866 B2
DATED : March 8, 2005
INVENTOR(S) : Tim Allen Kelly et al.

It is certified that error appears in the above-identified patent and that said Letters Patent is hereby corrected as shown below:

Column 29,
Line 56, "an" should read as -- pad --.

Signed and Sealed this

Thirtieth Day of August, 2005

JON W. DUDAS
*Director of the United States Patent and Trademark Office*